(12) United States Patent
Liu et al.

(10) Patent No.: US 7,122,319 B2
(45) Date of Patent: Oct. 17, 2006

(54) MULTIPLEXED IMMUNOHISTOCHEMICAL ASSAYS USING MOLECULAR TAGS

(75) Inventors: Linda Liu, Sunnyvale, CA (US); Po-Ying Chan-Hui, Oakland, CA (US); Hrair Kirakossian, San Jose, CA (US); Sharat Singh, San Jose, CA (US)

(73) Assignee: Monogram Biosciences, Inc, South San Francisco, CA (US)

( * ) Notice: Subject to any disclaimer, the term of this patent is extended or adjusted under 35 U.S.C. 154(b) by 512 days.

(21) Appl. No.: 10/702,269

(22) Filed: Nov. 5, 2003

(65) Prior Publication Data

US 2004/0121382 A1    Jun. 24, 2004

Related U.S. Application Data

(60) Provisional application No. 60/434,524, filed on Dec. 18, 2002.

(51) Int. Cl.
*C12Q 1/68* (2006.01)
*G01N 33/53* (2006.01)

(52) U.S. Cl. .......................... 435/6; 435/7.1; 536/23.1; 536/24.3

(58) Field of Classification Search .................. 435/6, 435/7.1; 536/23.1, 24.3
See application file for complete search history.

(56) References Cited

U.S. PATENT DOCUMENTS

| 4,725,537 A | 2/1988 | Fritsch et al. |
|---|---|---|
| 4,851,331 A | 7/1989 | Vary et al. |
| 5,403,711 A | 4/1995 | Walder et al. |
| 5,422,253 A | 6/1995 | Dahlberg et al. |
| 5,648,213 A | 7/1997 | Reddy et al. |
| 5,849,878 A | 12/1998 | Cantor et al. |
| 5,858,195 A | 1/1999 | Ramsey |
| 6,121,001 A | 9/2000 | Western et al. |
| 6,297,061 B1 | 10/2001 | Wu et al. |
| 6,335,201 B1 | 1/2002 | Albritton et al. |
| 6,540,895 B1 | 4/2003 | Spence et al. |
| 6,558,928 B1 | 5/2003 | Landegren |
| 6,613,525 B1 | 9/2003 | Nelson et al. |
| 6,627,400 B1 | 9/2003 | Singh et al. |
| 2002/0005354 A1 | 1/2002 | Spence et al. |
| 2002/0051986 A1 | 5/2002 | Baez et al. |
| 2002/0064779 A1 | 5/2002 | Landegren et al. |
| 2002/0142323 A1 | 10/2002 | Albritton et al. |

FOREIGN PATENT DOCUMENTS

| WO | WO 98/10267 | 3/1998 |
|---|---|---|
| WO | WO 99/131.8 | 9/1998 |

OTHER PUBLICATIONS

Giese, "Electrophoric Release tags: Ultrasensitive Molecular Labels Providing Multiplicity". Trends in Analytical Chemistry, vol. 2, No. 7, 1993.

(Continued)

*Primary Examiner*—Ethan Whisenant
(74) *Attorney, Agent, or Firm*—Jones Day

(57) ABSTRACT

Methods and compositions are provided for detection of analytes, such as cell surface moieties, preferably in multiplexed assays, such that multiple analytes can be assayed simultaneously. The methods employ analyte binding agents which are linked to oligonucleotide labels, which labels are then used for formation of cleavage structures and generation of detectable molecular tags. Preferably, multiple tags are generated per analyte binding event.

10 Claims, 11 Drawing Sheets

OTHER PUBLICATIONS

Joppich-Kuhn et al., "Release Tags: A new Class of Analytical Reagents" Clinical Cheistry, vol. 28, No. 9, 1982.

Levsky, et al, "Single-cell Gene Expression Profiling", Science, vol. 297, Aug. 2, 2002.

Chiem et al, "Microchip Systems for Immunoassay: An Integrated Immunoreactor with Electrophoretic Separation for Serum Theophylline Determination", Clinical Chemistry, 44:3, 591-598, 1998.

Krylov et al, "Instrumentation for Chemical Cytometry" Analytical Chemistry, Vo. 72, No. 4 Feb. 15, 2000.

Dixon, et al, "Gene-expression Analysis at the Singlecell Level", TiPS, vol. 21, Feb. 2000.

Freeman et al, "Analysis of Gene Expression in Single Cells", Current Opinion in Biotechnology, 10: 579-582.

Sims et al, "Single-cell Kinase Assays: Opening a Window onto Cell Behavior", Current Opinion in Biotechnology, 2003, 14: 23-28.

Fu et al, "A Microfabricated Fluorescence-activated Cell Sorter", Nature Biotechnology, vol. 17, Nov. 1999, 1109-1111.

Fu et al, "An Integrated Microfabricated Cell Sorter", Anal. Chem, 2002, 2451-2457.

Sims et al, "Micropipette Combination for Single-Cell Analysis", Anal Chem., 1998, 70,, 4570-4577.

Fishman et al, "Cell-to-Cell Scanning in Capillary Electrophoresis", Anal. Chem., 1996, 68, 1181-1186.

Krylov et al, "Single-Cell Analysis Using Capillary Electrophoresis: Influence of Surface Support Properties on Cell Injection into the Capillary", Electrophoresis 2000, 21, 767-773.

Chen et al, "Continuous Cell Introduction for the Analysis of Individual Cells by Capillary Electrophoresis",, Anal. Chem 2001, 73, 111-118.

Lillard et al, "Monitoring Exocytosis and Release from Individual Mast Cells by Capillary Electrophoresis with Laser-Induced Native Fluorescence Detection", Anal. Chem, 1996, 68, 2897-2904.

Li et al, "Transport Manipulation, and Reaction of Biological Cells on-Chip Using Electrokinetic Effects", Anal. Chem., 1997, 69, 1564-1568.

McClain et al, "Microfluidic Devices for the High-Throughput chemical Analysis of Cells", Anal. Chem, 2003, 75, 5646-5655.

Dittrich et al, "An Integrated Microfluidic System for Reaction High-Sensitivity Detection, and Sorting of Fluorescent Cells and Particles", Anal. Chem., 2003, 75, 5767-5774.

Joerger, et al, "Analyte Detection with DNA-Labeled Antibodies and Polymerase Chain Reaction", Clin. Chem., vol. 41, No. 9, 1995, 1371-1377.

Hendrickson, et al, "High Sensitivity Multianalyte Immunoassay Using Covalent DNA-Labeled Antibodies and Polymerase Chain Reaction", Nucleic Acids Research, 1995, vol. 23, No. 3, 522-529.

Lyamichev et al, "Plymorphism Identification and Quantitative Detection of Genomic DNA by Invasive Cleavage of Oligonucleotide Probes", Nature Biotechnology, vol. 17, Mar. 1999, 292-296.

Lyamichev et al, "Structure-Specfic Endonucleolytic Cleavage of Nucleic Acids by Eubacterial DNA Polymerases", Science, vol. 260, May 7, 1993, 778-783.

Sano et al, "Immuno-PCR: Very Sensitive Antigen Detection by Means of Specific Antibody-DNA Conjugates", Science, vol. 258, Oct. 2, 1992, 120-122.

Erdile et al, "Whole Cell ELISA for Detection of Tumor Antigen Expression in Tumor Samples", Journal of Imunological Methods, 258 (2001) 47-53.

Bator et al, "Measurement of Antibody Affinity for Cell Surface Antigents Using an Enzyme-linked Imunosorbent Assay", Journal of Imunological Methods, 125, (1989) 167-176.

Walker et al, "Isothermal in Vitro Amplification of DNA by a restriction Enzyme/DNA Polymerase System", Proc. Natl. Acad Sci. USA, vol. 89, Jan. 1992, 392-396.

MULTIPLEXED IMMUNOHISTOCHEMICAL ASSAYS USING MOLECULAR TAGS

CROSS-REFERENCE TO RELATED APPLICATIONS AND PATENTS

This application claims priority from U.S. provisional applications Ser. No. 60/434,524 filed 18 Dec. 2002, which application is incorporated herein by reference in its entirety.

FIELD OF THE INVENTION

The present invention relates to methods and compositions for detection of analytes, such as cell surface moieties, preferably in multiplexed assays, such that multiple analytes can be assayed simultaneously. In particular, the invention relates to multiplexed assays employing nucleic acid based generation of molecular tags.

REFERENCES

Bishop, G. A. and Hwang, J., *BioTechniques* 12(3):326–330 (1992).
Bator, J. M. and Reading, C. L., *J. Immunol. Methods* 125:167–176 (1989).
Chan, J. K., *Seminars in Diagnostic Pathology* 17(3): 170–7 (August 2000).
Emmert-Buck, M. R. et al., *Science* 274:998 (1996).
Goldstine, J. et al., *J. Neuropathology & Exp. Neurology* 61(8):653–662 (August 2002).
Grob, P. M. et al., *J. Biol. Chem.* 260:8044–8049 (1985)
Herlyn, M. et al., *Adv. Cancer Res.* 49:189–221 (1987)
Hoos, A. and Cordon-Cardo, C., *Laboratory Invest.* 81(10):1331–38 (October 2001).
Koprowski, H. et al., *Somat. Cell. Mol. Genet.* 11:297–302 (1985)
Lyamichev, V. et al., *Science* 260:778–783 (1993).
Murante et al., *J. Biol. Chem.* 270:30377 (1995).
Murthy, U. et al., *Arch. Biochem. Biophys.* 252:549–560 (1987).
O'Leary, T. J., *Applied Immunohistochemistry & Molecular Morphology* 9(1):3–8 (March 2001).
Zalipsky, S., *Bioconjugate Chemistry* 4:296–9 (1993).

BACKGROUND OF THE INVENTION

Biochemical species targeted in therapy or diagnosis frequently include cell surface antigens, which, upon recognition by natural or synthetic binding molecules, trigger a network of signal transduction and gene regulation events inside the cell that result in cellular responses important in the initiation or maintenance of a disease. Target antigens may also differentially reside on the surface of different cells and signify a unique state of physiology or disease progress in the tissue or organ.

Monoclonal antibodies directed against tumor-associated antigens expressed on the tumor cell surface have found application in the immunotherapy of human tumors. The interaction of certain monoclonal antibodies directed against tumor cells with cell surface antigens is well documented. See, e.g., Herlyn et al. (1987), Koprowski et al. (1985), Grob et al. (1985), and Murthy et al. (1987). Monoclonal antibodies targeted to the epidermal growth factor receptor (EGFR) are of great interest, due to the high level of expression of this receptor in patients with solid tumors. MAB have also been developed which target molecules implicated in other diseases, such as autoimmune diseases, AIDS, asthma, psoraisis, and other inflammatory disorders.

Target-specific binders such as antibodies are also widely employed in detection of such biological markers, particularly in differential assays of markers in different cell or tissue types, e.g. in immunohistochemical assays. Immunohistochemistry (IHC), which broadly includes techniques of screening for target analytes in multiple tissue or cell samples, such as tissue libraries, by application of known binding molecules followed by detection, can be used for detection of the presence or absence of molecular markers, typically proteins, involved in various stages of diseases, such as cancer. Methods have been developed for carrying out such assays on surface antigens in whole cells, as opposed to soluble antigens (see e.g. Bishop & Hwang, 1992; Bator & Reading, 1989). Over the last few years, the role of immunohistochemical analysis has been changing from that of an ancillary diagnostic technique to that of a stand-alone diagnostic method (O'Leary 2001). IHC studies play an increasingly important role in surgical pathology, and can be used, for example, in classifying tumors, predicting the origin of a carcinoma, demonstrating micrometastases and microorganisms, providing prognostic information, or rendering a diagnosis in a damaged specimen (Chan 2000).

In standard IHC assays, markers are generally detected by immunostaining of the specific binding molecules (e.g. antibodies) added to the sample. Consistency of interpretation of staining results, especially from one clinical setting to another, can be problematic. This technique also limits the number of different markers which can be detected simultaneously.

Many receptors are normally expressed on the cell surface to only a small extent, i.e. a few hundred to a few thousand receptors/cell. These include many receptors types of great medical interest, including, for example, receptors for granulocyte-macrophage colony-stimulating factor (GM-CSF), many interleukins, erythropoietin, and tumor necrosis factor (TNF). In addition, assays must often be carried out on tissue samples which are small, rare, unique, or otherwise limited in quantity. Accordingly, there is a need for methods of detecting such markers, often present at low levels, in limited tissue samples, where the method is quantitative, reproducible, and high sensitivity; that is, it gives a readily detectable signal from a small amount of analyte.

SUMMARY OF THE INVENTION

In one aspect, the invention provides a method of detecting the presence or absence of a plurality of analytes in a sample. The analytes may include, for example, cell receptors or other markers in a clinical tissue library.

In accordance with the method, there is provided, for each analyte being assayed, a binding composition, comprising a binding agent, such as an antibody, having a oligonucleotide label. For each oligonucleotide label is further provided a reagent pair, consisting of a detection probe specific for the oligonucleotide label in a given region, and a helper probe specific for the oligonucleotide label at a location adjacent to the given region. The detection probe has a molecular tag attached, where the molecular tag has distinct optical or separation properties with respect to molecular tags of other detection probes. In a preferred aspect, the tags are fluorescently labeled.

The binding compositions are combined with the sample so that analyte complexes are formed between the analytes and their respective binding compositions. Binding compositions that do not form analyte complexes (i.e. that do not bind to any analyte) are removed. Analyte complexes are then combined, under hybridization conditions, with a nuclease and the reagent pairs corresponding to the oligonucleotide label of each binding composition, such that the helper probe and detection probe specific for each oligonucleotide label form a cleavage structure with the oligonucleotide label that is recognized by the nuclease, and the nuclease cleaves the cleavage structure to release the molecular tag.

The released molecular tags are separated and identified to determine the presence or absence of the plurality of analytes. In one embodiment, each released tag has an electrophoretic mobility, upon release, which is distinct from electrophoretic mobility of released tags from other detection probes.

In a preferred aspect of the general method, the hybridization conditions are such that detection probe annealed to the oligonucleotide label is in equilibrium with unannealed detection probe, such that cleaved detection probe is repeatedly displaced from the oligonucleotide label by additional detection probe.

The method may also be carried out in a multiple binding event format, wherein at least one analyte has first and second binding sites. In this embodiment of the method, the binding composition provided for such analyte comprises a binding agent that is specific for the first binding site, and the helper probe provided for the binding composition is linked to a second binding agent that is specific for the second binding site. The binding composition may include, in this instance, a flexible linker between the binding agent and the oligonucleotide label; the helper probe may also be linked to the second binding agent via a flexible linker.

In a related aspect, a method is provided for detecting the presence or absence of a plurality of analytes in a sample, the method comprising the steps of:

providing, for each analyte, a binding pair comprising a first binding composition having a first oligonucleotide label, and a second binding composition having a second oligonucleotide label, where the first oligonucleotide label and the second oligonucleotide label are complementary to one another in a first region, such that whenever the first binding composition and the second binding composition bind to the same analyte, a duplex is formed;

providing, for each first oligonucleotide label and second oligonucleotide label, a detection probe specific for either the first oligonucleotide label or the second oligonucleotide label at a location adjacent to the region, the detection probe having a molecular tag attached by a cleavable linkage, the molecular tag of each detection probe having one or more physical and/or optical characteristics distinct from those of molecular tags attached to other detection probes, so that upon separation each molecular tag forms a distinguishable peak in a separation profile;

combining the binding pairs with the sample, such that analyte complexes are formed between the analytes and their respective binding pairs and duplexes are formed between each first and second oligonucleotide labels;

removing binding pairs that do not form analyte complexes;

combining under hybridization conditions: a nuclease, the analyte complexes, and the detection probes of each binding pair, such that the detection probes specific for each first or second oligonucleotide label form a cleavage complex recognized by the nuclease, and such that the nuclease cleaves and releases the molecular tags from cleavage complexes; and separating and identifying the released molecular tags to detect the presence or absence of the plurality of analytes.

DETAILED DESCRIPTION OF THE INVENTION

I. Definitions

Figure 1A:
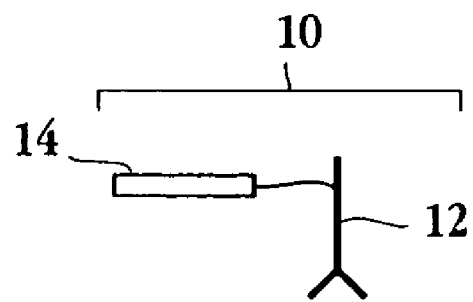
FIG. 1A is a schematic illustration of an antibody-oligonucleotide conjugate, one embodiment of a binding composition having an oligonucleotide label.

Unless otherwise defined below, the terms used herein have their normally accepted scientific meanings. Definition of standard chemistry terms may be found in reference works, including Carey and Sundberg (1992) "Advanced Organic Chemistry $3^{rd}$ Ed.", Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. Such techniques are explained fully in the literature. See, for example, G. Barany and R. B. Merrifield (1980), "The Peptides: Analysis, Synthesis, Biology", Vol. 2, E. Gross and J. Meienhoffer, eds., Academic Press, New York.; *Methods In Enzymology* (S. Colowick and N. Kaplan, eds., Academic Press, Inc.); *Remington's Pharmaceutical Sciences,* 18th Edition (Easton, Pa.: Mack Publishing Company, 1990).

All publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an oligonucleotide" includes a mixture of two or more oligonucleotides, and the like.

In describing the present invention, the following terms will be employed, and are intended to be defined as indicated below.

A "binding composition having a oligonucleotide label" or simply "binding composition", as used herein, refers to a ligand, or binding agent, employed in a binding assay, e.g. an antibody, which is conjugated, preferably covalently, to a known-sequence oligonucleotide. The oligonucleotide label may also be referred to herein as a template oligonucleotide. Such a composition may also be referred to herein as a "ligand-oligonucleotide conjugate".

A "detection probe" refers to a chemical structure containing (1) a molecular "tag" and (2) a known-sequence oligonucleotide. Sets of probes, having a known correlation between oligonucleotide sequence and tag identity, are generally provided for use in the methods described herein. The known-sequence oligonucleotide is designed to be partially complementary to a region of a selected oligonucleotide label in a binding composition (defined above), in a manner described further below. Cleavage of the probe, when it is bound to the oligonucleotide label, releases the molecular tag (also referred to, in the case of electrophoretic tags, as eTags, eTag reporters, or eTag markers), which contains a detectable label and a mobility modifying group. The released molecular tag may contain a portion of the probe oligonucleotide as well. Molecular tags are described in detail in Section IIIB. Preferably, multiple cleavages of bound detection probes result from a single analyte binding event, thereby generating multiple molecular tags for detection, as discussed further below.

A "helper probe" or "primer" is an oligonucleotide which is designed to be partially or fully complementary to a region of a selected oligonucleotide label in a binding composition (defined above). The presence of the helper probe generally enhances cleavage of the detection probe when both are bound to an oligonucleotide label in a cleavage structure.

As used herein, "probe" may refer to "helper probe" (e.g. primer), "detection probe" and/or "electrophoretic probe", either each alone or collectively, depending on context.

A "cleavage structure" refers to a complex of a template oligonucleotide, such as an oligonucleotide label, with a detector probe and, typically, a helper probe, which is recognized by a nuclease, such that the detector probe is cleaved, releasing a detectable molecular tag. In accordance with the methods described herein, the detector probe is not cleaved unless it is incorporated into a cleavage structure. The cleavage structure comprising the detection probe may also be referred to as a "recognition duplex".

"Adjacent", with respect to regions of an oligonucleotide label, includes regions which are contiguous, i.e. having no intervening nucleotides, but may also include proximal regions, typically having up to three, preferably two, and more preferably one intervening nucleotide.

As used herein, the term "label" or "detectable label", as a component of a detection probe or molecular tag, refers to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. The term "fluorescer" refers to a substance or a portion thereof which is capable of exhibiting fluorescence in the detectable range.

As used herein, the term "spectrally resolvable", in reference to a plurality of fluorescent labels, means that the fluorescent emission bands of the labels are sufficiently distinct, i.e. sufficiently non-overlapping, that molecular tags to which the respective labels are attached can be distinguished on the basis of the fluorescent signal generated by the respective labels using standard photodetection systems, e.g. employing a system of band pass filters and photomultiplier tubes, or the like, as exemplified by the systems described in U.S. Pat. Nos. 4,230,558, 4,811,218, or the like, or in Wheeless et al., in Flow Cytometry: Instrumentation and Data Analysis (Academic Press, New York, 1985), pp. 21–76.

"Electrophoretic mobility" refers to the mobility of a charged compound through a defined separation medium, and under defined buffer and electric field conditions. "Different electrophoretic mobilities," as applied to molecular tags, means that the tags are separable from one another on the basis of different rates of migration in a given electrophoretic medium, e.g., acrylamide gel, and under defined electrophoretic conditions, e.g., standard electrophoretic conditions for separating either positively or negatively charged compounds with different charge/mass ratios.

"Electrophoretic resolution" is a measure of the distinctness, or lack of overlap, of adjacent peaks in an electropherogram. It can be defined, for example, as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like.

As used herein, a "solid support" refers to a solid surface such as a magnetic bead, latex bead, microtiter plate well, glass plate, nylon, agarose, acrylamide, and the like.

A "protein" or a "polypeptide" is used in its broadest sense to refer to a compound of two or more subunit amino acids, amino acid analogs, or other peptidomimetics. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced.

"Antibody" refers to an immunoglobulin that specifically binds to, and is thereby defined as complementary with, a particular spatial and polar organization of another molecule. The antibody can be monoclonal or polyclonal and can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular target is maintained.

A "monoclonal antibody" (MAB) is an immunoglobulin produced by a single clone of lymphocytes, i.e. the progeny of a single B cell, which recognizes only a single epitope on an antigen. Antibodies are discussed further in Section VI.A below.

"Capillary electrophoresis" refers to electrophoresis in a capillary tube or in a capillary plate, where the diameter of the separation column or thickness of the separation plate is between about 25–500 microns, allowing efficient heat dissipation throughout the separation medium, with consequently low thermal convection within the medium.

A "sieving matrix" or "sieving medium" refers to an electrophoresis medium that contains crosslinked or non-crosslinked polymers which are effective to retard electrophoretic migration of charged species through the matrix.

"Specific", in reference to the binding of two molecules or a molecule and a complex of molecules, refers to the specific recognition of one for the other and the formation of a stable complex, as compared to substantially less recognition of other molecules and the lack of formation of stable complexes with such other molecules. Preferably, "specific", in reference to binding, means that to the extent that a molecule forms complexes with other molecules or complexes, it forms at least fifty percent of the complexes with the molecule or complex for which it has specificity. Generally, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so forth.

A "multiplexed assay" refers to an assay in which multiple assay reactions, e.g. simultaneously assays of multiple analytes, are carried out in a single reaction chamber and/or and analyzed in a single separation and detection format.

An "analyte" refers to a substance, compound, or component in a sample whose presence or absence is to be detected or whose quantity is to be measured. Analytes include but are not limited to peptides, proteins, oligonucleotide labels, polypeptides, oligonucleotides, organic molecules, haptens, epitopes, parts of biological cells, post-translational modifications of proteins, receptors, complex sugars, vitamins, hormones, and the like. There may be more than one analyte associated with a single molecular entity, e.g. different phosphorylation sites on the same protein. Likewise, there may be more than one molecular entity associated with a single analyte, e.g. different cell surface membrane receptor proteins that form dimers.

"Chromatography" or "chromatographic separation" as used herein refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like.

"High pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 µm packed into the separation column, (iii) takes place at a temperature in the range of from 35° C. to 80° C. and at column pressure up to 150 bars, and (iv) employs a flow rate in the range of from 1 µL/min to 4 mL/min. Solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2/g$, and (iv) having a bonding phase density (i.e. the number of retention ligands per unit area) in the range of from 1 to 5 per $nm^2$.

"Capillary electrochromatography" ("CEC") refers to a liquid phase chromatographic technique in which fluid is driven by electroosmotic flow through a capillary-sized column, e.g. with inside diameters in the range of from 30 to 100 µm. CEC is disclosed in Svec, *Adv. Biochem. Eng. Biotechnol.* 76: 1–47 (2002); Vanhoenacker et al., *Electrophoresis* 22: 4064–4103 (2001); and like references. CEC column may used the same solid phase materials as used in conventional reverse phase HPLC and additionally may use so-called "monolithic" non-particular packings. In some forms of CEC, pressure as well as electroosmosis drives an analyte-containing solvent through a column.

"Isothermal", in reference to assay conditions, means a uniform or constant temperature at which cleavage of probe, in accordance with the present invention, is carried out. The temperature is chosen so that the duplex formed by hybridizing the probes to a oligonucleotide label having a target oligonucleotide label sequence is in equilibrium with the free or unhybridized probes and free or unhybridized target oligonucleotide label sequence, a condition that is otherwise referred to herein as "reversibly hybridizing" the probe with an oligonucleotide label. Normally, at least 1%, preferably 20 to 80%, usually less than 95% of the oligonucleotide label is hybridized to the probe under the isothermal conditions. Accordingly, under isothermal conditions molecules of oligonucleotide label that are hybridized with the probes, or portions thereof, are in dynamic equilibrium with molecules that are not hybridized with the probes. Some fluctuation of the temperature may occur and still achieve the benefits of the present invention. The fluctuation generally is not necessary for carrying out the methods of the present invention and usually offers no substantial improvement.

Accordingly, the term "isothermal" includes the use of a fluctuating temperature, particularly random or uncontrolled fluctuations in temperature, but specifically excludes the type of fluctuation in temperature referred to as thermal cycling, which is employed in some known amplification procedures, e.g., polymerase chain reaction.

"Melting temperature", or Tm, is defined as the temperature at which 50% of a given nucleic acid duplex has melted (i.e., has become single-stranded). The Tm is dependent on reaction conditions such as the salt concentration of the solution. The desired Tm is typically achieved by manipulation of the length and nucleotide base composition of the complementary regions. Other methods can also be utilized to adjust duplex Tm, including but not limited to incorporation of mismatches, replacement of some or all of the complementary basepairs with stability enhancing nucleotides or internucleotide linkages, e.g. peptide nucleic acids, phosphoramidates, 2'-methoxyribonucleosides, and the like.

Several equations for calculating the Tm of nucleic acids are well known in the art. As indicated by standard references, a simple estimate of the Tm value may be calculated by the equation. $Tm=81.5+0.41$ (% G+C) when a nucleic acid is in aqueous solution at 1 M NaCl (see e.g., Anderson and Young, Quantitative Filter Hybridization, in Nucleic Acid Hybridization (1985)). Other references (e.g., Allawi, H. T. & SantaLucia, J., Jr., *Biochemistry* 36, 10581–94 (1997)) include alternative methods of computation which take structural and environmental factors, as well as sequence characteristics, into account for the calculation of Tm.

"Specific" or "specificity", in reference to the binding of one molecule to another molecule, such as a probe for a target oligonucleotide label, refers to the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among oligonucleotide labels and/or oligonucleotides, receptor-ligand interactions, and the like. As used herein, "contact" in reference to specificity or specific binding means two molecules are close enough so that short range non-covalent chemical interactions, such as Van der Waal forces, hydrogen bonding, hydrophobic interactions, and the like, dominate the interaction of the molecules.

"Sample" as used herein includes a specimen or culture (e.g., microbiological culture) as well as other biological or environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Separation profile" in reference to the separation of molecular tags means a chart, graph, curve, bar graph, or other representation of signal intensity data versus time, or other variable related to time, that provides a readout, or measure, of the number of molecular tags of each type produced in an assay. A separation profile may be an electropherogram, a chromatogram, an electrochromatogram, or like graphical representations of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths.

II. Assay Formats

The methods of the invention can be used to determine the presence of an analyte or analytes in a sample. Typically, the sample contains at least one cell type, and the analytes may be cell surface moieties, such as cell surface receptors.

In general, binding of a ligand, or binding agent, to an analyte is followed, as described below, by release of one or more detectable molecular tags which can be correlated with the identity of the binding agent. According to one aspect of the invention, the binding agent is conjugated to an oligonucleotide label, and the oligonucleotide label is one component of a nucleic acid-based signal amplification system. Signal is amplified by virtue of repeated cycles of (i) binding of a detection probe to the oligonucleotide label, (ii) cleavage of the probe to release molecular tag(s), and (iii) replacement of cleaved probe by intact probe, as described further below. By detecting the type and amounts of released "tags", information about the presence or absence of different analytes in the sample can be obtained.

The binding agent may be, for example, an antibody, particularly a monoclonal antibody, or a peptide ligand, such as a secreted peptide. Antibodies are discussed in more detail below. Receptor binding compounds may be agonists (which produce a physiologic reaction similar to that of a naturally occurring receptor binding ligand) or antagonists (which interfere with the physiological action of the receptor).

The assays described herein are particularly useful for detecting binding to low levels of analytes in a sample, or analytes in small samples, with limited consumption of the sample. Examples include tissue samples obtained by techniques such as laser-capture microdissection (e.g. Emmert-Buck et al., 1996), which can provide very pure and representative cell samples, but which are limited in size. Other limited samples included those in tissue libraries obtained from patient populations, e.g. in clinical studies. Such libraries frequently comprise cancer tissue samples, although other types of specimens can be collected, as in brain tissue libraries for studies of neurodegenerative diseases (see e.g. Goldstine et al., 2002).

In accordance with the method, a sample is provided which may contain one or more analytes to be assayed. The method may be used to detect the presence and/or level of selected analytes, by employing ligands, e.g. antibodies, which are known to bind to these analytes. Alternatively, the method may be used to screen candidate ligands for binding to known targets. The method is particularly suited for the first type of assay, particularly when the analytes are suspected to be present at a low level and/or the amount of available sample is small.

Each binding agent is provided in the form of a ligand-oligonucleotide conjugate, also referred to herein as a binding composition, such as shown schematically at 10 in FIG. 1A where the binding agent is an antibody. Each different binding agent (12) is conjugated to a different known-sequence oligonucleotide (14) to form the conjugate. One or, preferably, a plurality of such conjugates is added to the sample, under conditions such that binding occurs between analytes in the sample and ligands for which they have a binding affinity, forming one or more analyte complexes.

Figure 1B:
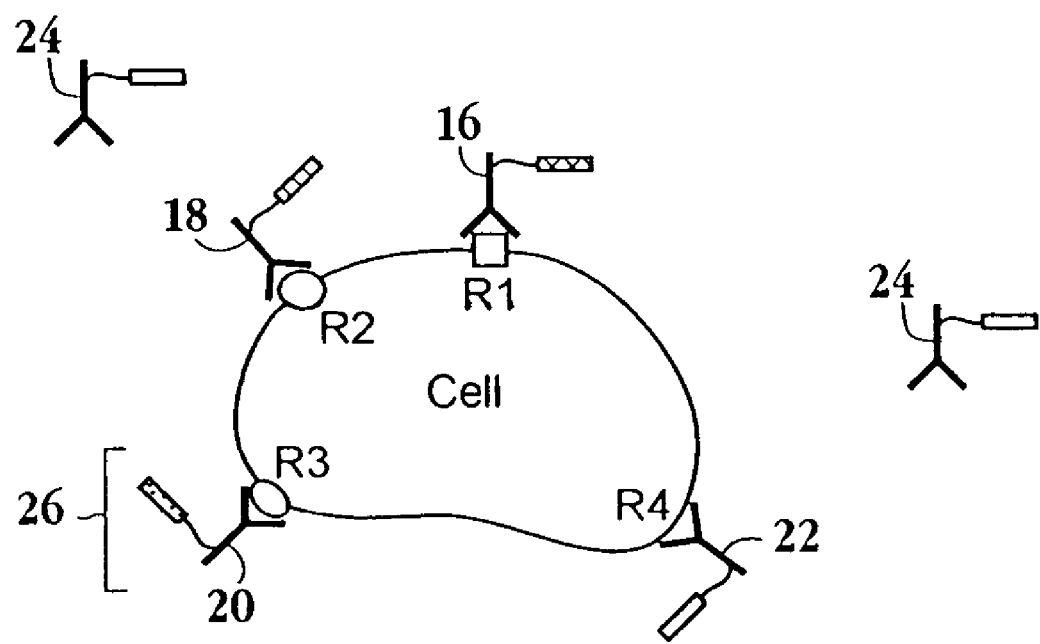
FIG. 1B is a schematic illustration of several different antibody-oligonucleotide conjugates, where each different antibody is conjugated to a different known-sequence oligonucleotide label, and binding of a subset of these conjugates to target moieties on a cell surface.

In one embodiment, the sample includes at least one cell type; the analytes may thereby include cell-surface receptors. FIG. 1B illustrates a cell having receptors R1, R2, R3, and R4. In the system illustrated, five different ligand-oligonucleotide conjugates 16, 18, 20, 22, and 24, each binding agent bearing a different sequence oligonucleotide, are added to a sample containing the cell. The antibody components of conjugates 16, 18, 20, and 22 bind to receptors R1, R2, R3, and R4, respectively, as shown, forming analyte complexes such as 26, while conjugate 24 remains unbound.

Figure 1C:
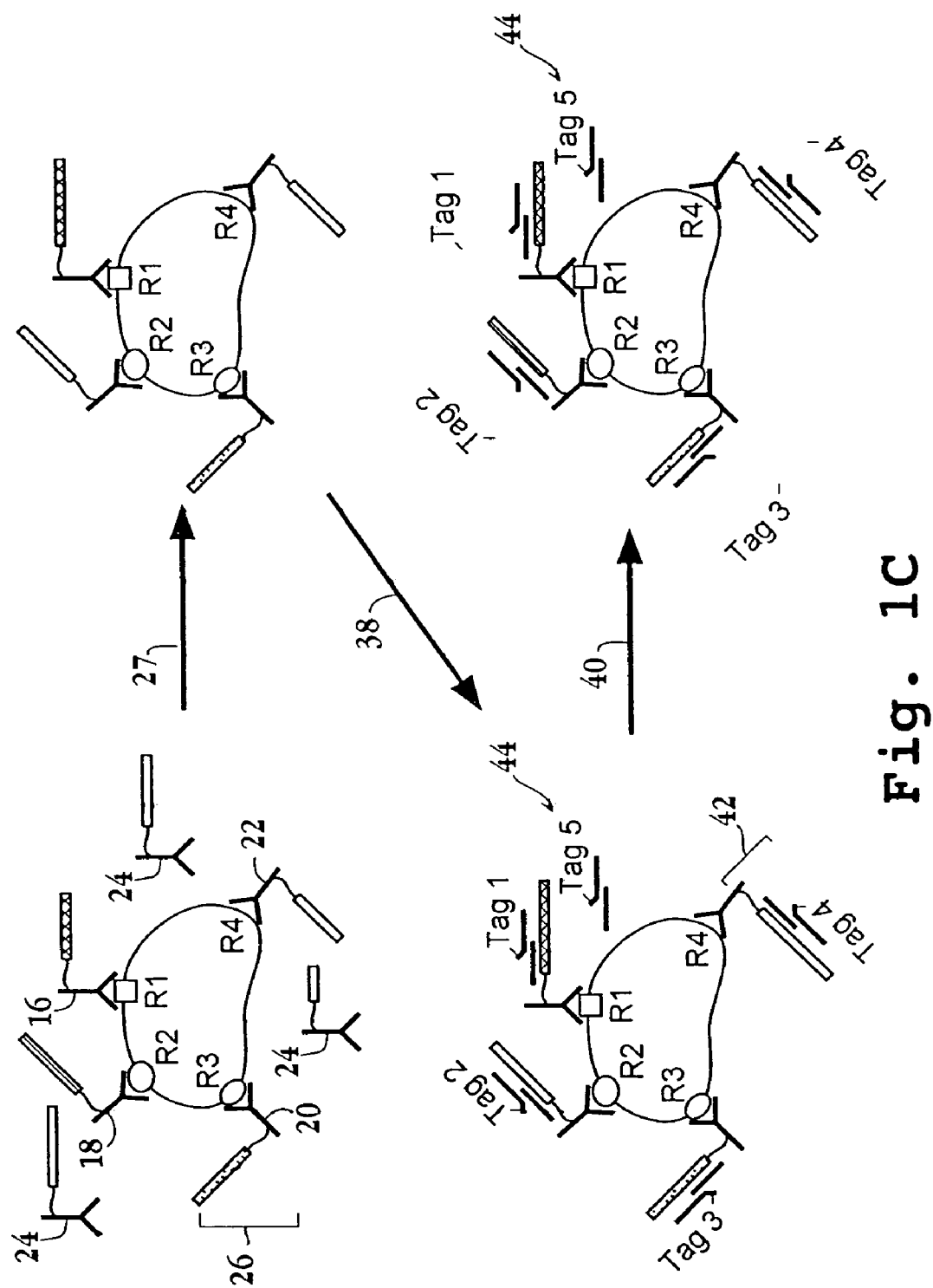
FIG. 1C illustrates steps in an assay method in accordance with the invention, for detecting binding between several ligands having oligonucleotide labels and several target cell surface moieties, including a typical electropherogram (FIG. 1D) of cleaved molecular tags resulting from such an assay.

With reference to FIG. 1C, bound ligand-oligonucleotide conjugates, also referred to herein as analyte complexes, formed between the analytes and their respective binding compositions, are then separated (27) from unbound ligand-oligonucleotide conjugates, such as 26. Separation can be achieved in a variety of ways, each employing a reagent bound to a solid support that distinguishes between binding and non-binding conjugates. The solid support may be a vessel wall, e.g., microtiter well plate well, capillary, plate, slide, beads, including magnetic beads, liposomes, or the like. The primary characteristics of the solid support are that it (1) permits segregation of the binding moieties from non-binding moieties, preferably by noncovalent binding, and (2) does not interfere with the formation or stability of the analyte complex, nor the other operations of the determination. This can be accomplished, for example, by employing ligand-oligonucleotide conjugates which comprise an affinity molecule, such as biotin, and capturing cells containing bound ligands on a surface containing a binding partner for the affinity molecule, such as streptavidin.

The non-binding cells and/or unbound binding agent are generally removed by washing the support. Where particles or beads are employed, these may be separated from the supernatant before washing, by methods such as filtration, centrifugation, or magnetic separation.

Alternatively, a secondary antibody conjugated to a reagent such as biotin may be added, to bind the antibody portion of nonbinding conjugates, such as 24, which are not part of analyte complexes. The biotinylated conjugates can then be removed by contacting the mixture with a streptavidinated solid phase support, leaving the analyte complexes in solution.

Other components of the assay include a nuclease, as described further below, and one or more detection probes, or, more typically, one or more detection probe/helper probe pairs, where each pair corresponds in a known manner to one of the ligand-oligonucleotide conjugates. Each pair comprises (i) a helper probe specific for the oligonucleotide label of the conjugate, in a given region, and (ii) a detection probe specific for the oligonucleotide label of the conjugate, at a second region which may be contiguous to the given region. The probe also includes a molecular tag, having distinct optical and/or separation properties, such as mass or electrophoretic mobility, with respect to molecular tags of other probes. Such tags are described further in Section IIIB below.

The oligonucleotides used for the oligonucleotide label of the binding composition, the detection probe, and the helper probe or primer are effective to hybridize in a sequence-specific matter to form a cleavage structure, which is a substrate for the cleavage enzyme employed in the assay. Typically, phosphodiester-linked deoxyribooligonucleotides (DNA) are used, although RNA oligomers also form cleavage structures and thus may be employed (see e.g. Lyamichev et al., 1993; Brow et al., U.S. Pat. No. 6,001,567). Examples of cleavage structures are described in more detail in Section III below.

The probes are designed to react with the desired target oligonucleotide label(s) and preferably to not react with any non-target oligonucleotide label(s) (i.e., cross-react). However, in general, if one probe of a detector/helper pair hybridizes with an undesired target but the other does not, the assays will still function properly, since both probes must hybridize in order for the cleavage structure to be formed, as discussed further below.

Figure 2A:
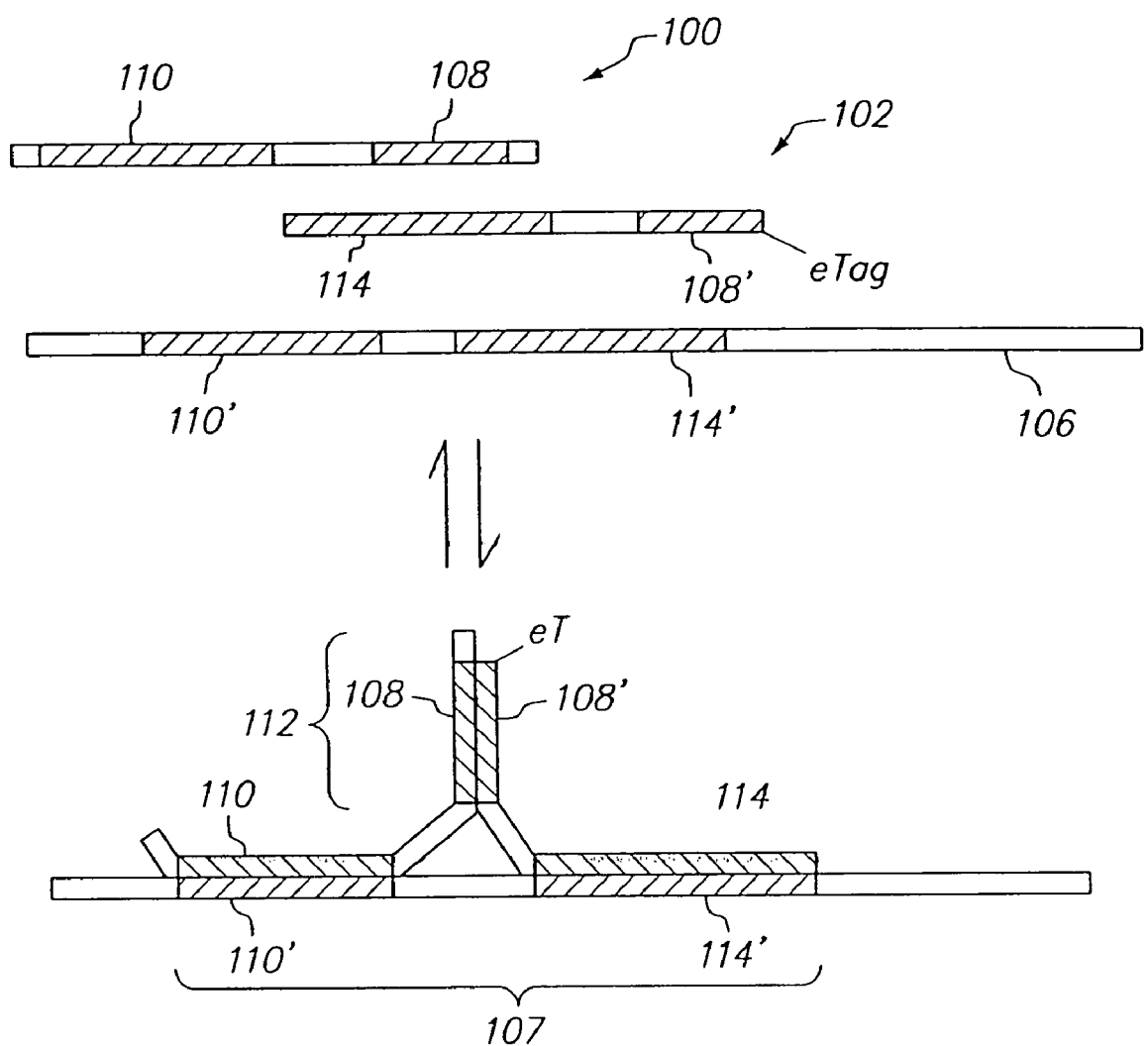
FIG. 2A illustrates an example of the combination of a helper probe and a detection probe with a target oligonucleotide label, to form a stable complex containing a recognition duplex.
Figures 3A, 3B:
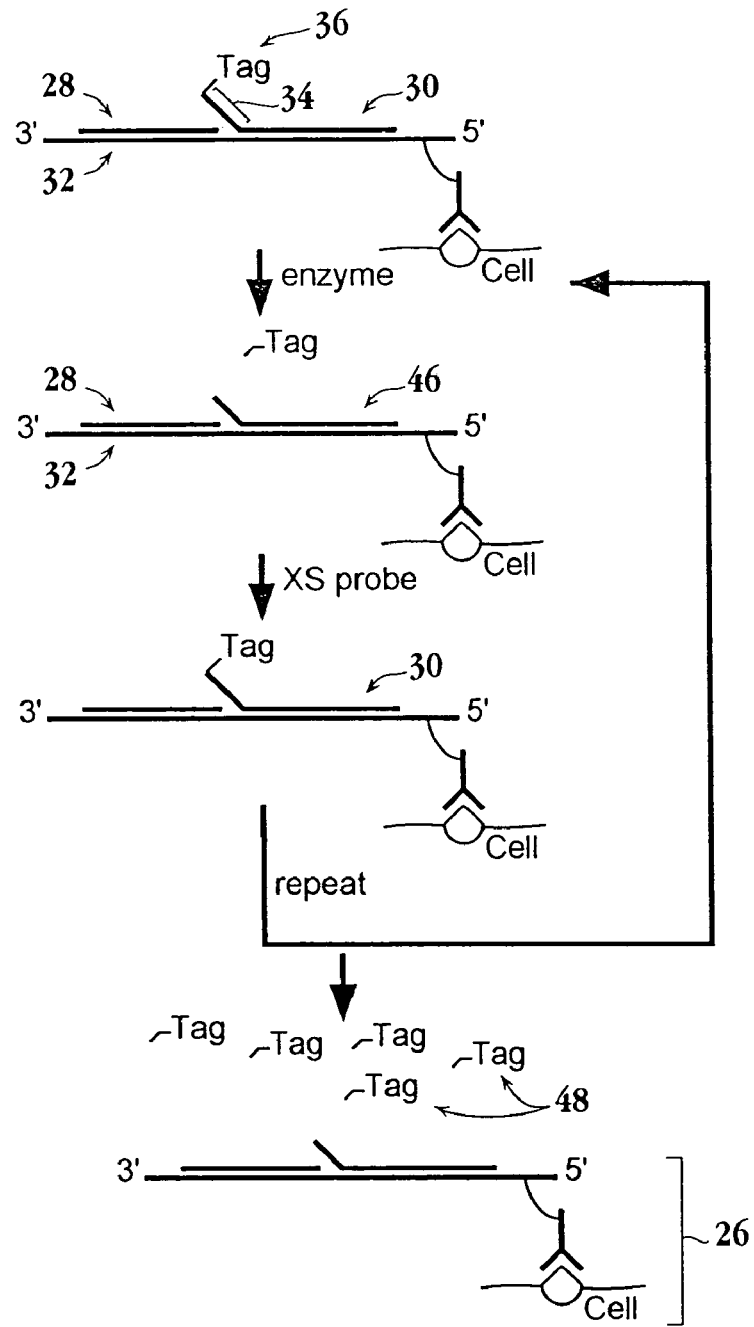
FIG. 3A is a diagram of an exemplary cleavage structure formed from a helper probe oligonucleotide, a molecular tag-labeled detection probe oligonucleotide, and the oligonucleotide label component of an antibody-oligonucleotide complex.
FIG. 3B illustrates generation of multiple cleaved molecular tags from a single analyte complex.
Figure 4A:
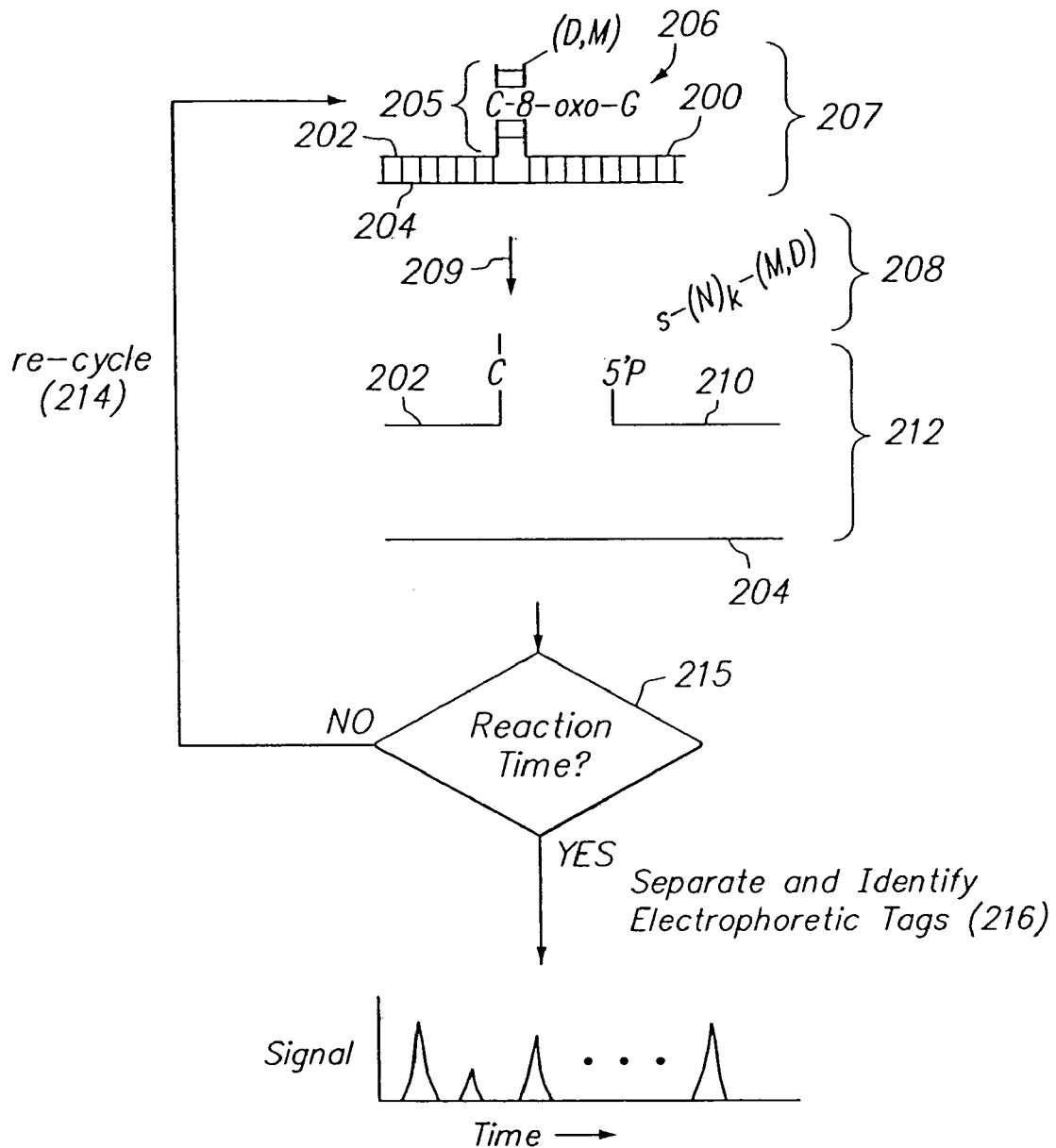
FIG. 4A illustrates an example of an assay in accordance with the invention in which the cleavage agent is hOGG1 protein.

To detect target oligonucleotide labels in a sample using such pairs of helper and detection probes, the following general procedure is used: 1) the pairs of helper and detection probes are added to the sample containing bound ligand-oligonucleotide label complexes, 2) the mixture is incubated to allow annealing of the appropriate regions to occur, 3) the cleavage structures are cleaved by an appropriate enzyme to release molecular tags, and 4) the released tags are separated and identified, to identify the corresponding ligand-oligonucleotide complexes, and thus the corresponding analytes. Exemplary types of cleavage structures (e.g. as shown in FIGS. 2A, 3A, and 4A) are described in further detail below.

A nuclease can also cleave other bonds in the detection probe that are nuclease-susceptible. An advantage of having at least one nuclease-resistant bond in the detection probe is that a tagged probe will yield a single sized species of released tag reporter upon cleavage. Nuclease-cleavable bonds can include, for example, a phosphodiester bond, and nuclease-resistant bonds can include, for example, thiophosphate, phosphinate, phosphoramidate, or a linker other than a phosphorous acid derivative, such as amide and boronate linkages.

Annealing conditions used for formation of the cleavage structures can be varied depending on the exact application, the design of the probe, the nature of the oligonucleotide label, and the composition of the sample in which the target oligonucleotides are contained. Factors known to influence the rate of nucleic acid hybridization include the concentration of the nucleic acids, the temperature at which the assay is performed, and the concentration of salts and/or other charge-shielding ions in the assay solution. Optimal conditions may vary based on the sample type (e.g., purified genomic DNA, body fluid extract, lysed bacterial extract), and can adjusted accordingly by one of skill in the art.

Buffer conditions are chosen to include a sufficient salt concentration to allow hybridization at the desired temperature and concentration ranges, and to be compatible with the enzyme. For enzymes obtained commercially, the manufacturer's instructions generally provide recommended buffers. Generally, conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The oligonucleotides (detector probe oligonucleotide and helper probe or primer oligonucleotide) are preferably provided in sufficient excess such that the rate of hybridization to the target oligonucleotide label is rapid. Suitable concentrations are in the range of 0.1 nM to 10 µM, preferably 1 nM to 10 µM. As discussed further below, the probe and optionally the primer oligonucleotide are preferably provided in excess relative to the oligonucleotide label. It should be noted that increasing the concentration of the probe causes the reaction rate to approach a limiting value that depends on probe sequence, temperature, concentration of oligonucleotide label sequence and enzyme concentration. For many detection methods, very high concentrations of the probe may make detection more difficult. If accurate detection of cleaved probe is compromised by large amounts of uncleaved probe, the concentration of probe should be reduced, or the uncleaved probe may be removed from the assay mixture prior to analysis.

A nuclease is generally present in an amount sufficient to cause the cleavage of the detector oligonucleotide, when it is reversibly hybridized to the oligonucleotide label, to proceed at least half as rapidly as the maximum rate achievable with excess enzyme, preferably, at least 75% of the maximum rate. Several nucleases that can be used to cleave different types of nucleic acids are known in the art, as discussed in more detail below. For example, nucleases are available that can cleave double-stranded DNA, for example, DNAse I and Exonuclease III, or single-stranded DNA, for example, nuclease S1. Nucleases include enzymes that function solely as nucleases as well as multi-functional enzymes that contain nuclease activity such as, for example, DNA polymerases like Taq polymerase that have 5' nuclease activity. Several derivatives of Taq polymerases derived from different bacterial species or from designed mutations are known which cleave specific structures of nucleic acid hybrids (Kaiser et al., *J. Biol. Chem.* 274:21387–21394 (1999); Lyamichev et al., *Proc. Natl. Acad. Sci. USA* 96:6143–6148 (1999); Ma et al., *J. Biol. Chem.* 275:24693–24700 (2000)).

The concentration of the nuclease is usually determined empirically. Preferably, a concentration is used that is sufficient such that further increase in the concentration does not decrease the time for the amplification by over 5-fold, preferably 2-fold. The primary limiting factor generally is the cost of the reagent. In this respect, then, the oligonucleotide label and the enzyme are generally present in a catalytic amount.

The assays are carried out in an aqueous medium at a pH typically in the range of about 4.5 to 9.5, more usually in the range of about 5.5–8.5, and preferably in the range of about 6–8. The pH and temperature are chosen so as to achieve the reversible hybridization or equilibrium state under which cleavage of a probe occurs, in accordance with the present invention. In some instances, a compromise is made in the reaction parameters in order to optimize the speed, efficiency, and specificity of the steps of the present method. Illustrative buffers that may be used include borate, phosphate, carbonate, Tris, barbital and the like. The particular buffer employed is not critical to the invention but in individual methods one buffer may be preferred over another.

Assay reactions in accordance with the present invention are carried out under isothermal conditions, generally carried at a temperature that is near the melting temperature of the probe:oligonucleotide label complex. Accordingly, the temperature employed depends on a number of factors. Usually, for cleavage of the probe in accordance with the present invention, the temperature is about 35° C. to 90° C., depending on the length and sequence of the probe. It will usually be desired to use relatively high temperature of 60° C. to 85° C. to provide for a high rate of reaction. The exact temperature utilized also varies depending on the salt concentration, pH, solvents used, and the length of and composition of the target oligonucleotide label sequence as well as the probe as mentioned above. It is understood that the selection of optimal reaction temperature also takes into account the temperature dependence of the nuclease being employed.

The assays are preferably carried out a temperature slightly below the $T_m$ of the least stable duplex formed in the reaction. Melting temperatures for the oligonucleotides and for their component regions can be determined empirically, estimated through the use of computer software as known in the art, or, for oligonucleotides about 10–30 nucleotides in length, approximated by assigning 2° C. per A-T basepair and 4° C. per G-C basepair. If non-specific cleavage (i.e., cleavage of the probe at many or all positions along its length) is detected, a higher temperature should be employed; conversely, if little or no cleavage occurs, a lower temperature should be used. In a preferred embodiment, the assay temperature is slightly above the $T_m$ of the region of the probe oligonucleotide that anneals to the oligonucleotide label, so that multiple cleavages can occur rapidly. Typically, the incubation temperature is preferably between 5° and 70° C., preferably between 30° and 65° C. Generally, the time for incubation after combination of all or a portion of the reagents, for each step of the assay, is at least 5 minutes, more usually at least 15 minutes.

In one aspect of the invention, released molecular tags accumulate because of the equilibrium exchange or cycling of detection probes between the bound state in a structure and a free state in solution. In another aspect, cleavage of the nucleic acid structure accelerates disassociation by destabilization of the structures, e.g. by creating two short duplexes in place of a single long duplex. In both cases, dissociation frees an oligonucleotide label for a new cycle of structure formation and cleavage, thereby permitting the accumulation of released molecular tags.

Guidance for selecting assay conditions and oligonucleotide sequences for forming the above complexes between helper probes, detection probes, and target oligonucleotide labels can be found in the art, e.g. Hogan et al., U.S. Pat. No. 5,451,503; Western et al., U.S. Pat. No. 6,121,001; Reynaldo et al., *J. Mol. Biol.* 297: 511–520 (2000); and Wetmur, *Critical Rev. in Biochem. Mol. Biol.*, 26: 227–259 (1991); each of which is hereby incorporated by reference.

III. Formation and Cleavage of Cleavage Structures

A. General

As discussed above, the assays of the invention employ nucleic acid-based means for generating molecular tags, and for amplifying signal produced as a result of a binding event. In general, the assays employ formation of a complex having the general elements (analyte-binding agent-nucleic acid-based molecular tag generator). The nucleic acid-based molecular tag generator amplifies signal by virtue of repeated cycles of (i) binding of a detection probe to an oligonucleotide label on the binding agent, (ii) cleavage of the probe to release molecular tag(s), and (iii) replacement of cleaved probe by further intact detection probe. Selected examples of such nucleic acid cleavage protocols are described below and illustrated in the accompanying drawings.

Several nucleic acid-based signal amplification techniques may be used with the invention to generate molecular tags, including techniques employing probe degradation and techniques employing probe synthesis or ligation, e.g. Schweitzer et al., Nature Biotechnology 20: 359–365 (2002); Martinelli et al., U.S. Pat. No. 6,083,689; Fredriksson et al., Nature Biotechnology 20: 473–477 (2002), and the like. In one aspect, signals based on released molecular tags may be generated by any one of several nucleic acid-based signal amplification techniques that use the degradation of a probe with a nuclease activity, including but not limited to "taqman" assays, e.g. Gelfand, U.S. Pat. No. 5,210,015; probe-cycling assays, e.g. Brow et al., U.S. Pat. No. 5,846,717; Walder et al., U.S. Pat. No. 5,403,711; Hogan et al., U.S. Pat. No. 5,451,503; Western et al., U.S. Pat. No. 6,121,001; Fritch et al., U.S. Pat. No. 4,725,537; Vary et al., U.S. Pat. No. 4,767,699; and other degradation assays, e.g. Okano and Kambara, Anal. Biochem. 228: 101–108 (1995). In particular, several such signal amplification techniques for generating molecular tags are disclosed in Singh, U.S. Pat. No. 6,322,980; Singh, International patent publication WO 00/66607; and Matray et al., U.S. patent publications 2002/0146726 and 2002/0142329. All of the U.S. patents cited in this paragraph are incorporated by reference for their disclosure of nucleic acid-based signal amplification techniques.

In one aspect, the invention employs signal generation techniques that use the coordinated operation of a helper probe and a detection probe on a localized region of an oligonucleotide label to create a cleavage structure, or complex, that serves as a substrate for a nuclease. Once such a complex is formed under assay conditions, it is recognized by a nuclease, which then cleaves the detection probe in the complex to release a molecular tag. Assay conditions are such that a cleavage structure will not form, that is, the detection probe will not release the molecular tag, in the absence of the oligonucleotide label.

Briefly, such methods employ the following steps, for detecting one or more oligonucleotide labels. As described above, each oligonucleotide label is part of a binding composition which also includes an analyte-specific ligand. The steps include:

(i) providing for each oligonucleotide label a detection probe complementary to a region of the oligonucleotide label and, in many instances, a helper probe complementary to the oligonucleotide label adjacent to said region, each detection probe having a molecular tag attached by a cleavable linkage, and the molecular tag of each detection probe having one or more physical and/or optical characteristics distinct from those of molecular tags attached to other detection probes so that each molecular tag forms a distinguishable peak in a separation profile of such tags;

(ii) mixing under hybridization conditions a nuclease, the sample, the detection probes, and optionally the helper probes to form an assay mixture, such that the probe(s) hybridized to the oligonucleotide labels are recognized by the nuclease in a reaction that results in the detection probe being cleaved at a cleavage site, so that the assay mixture contains released molecular tags, uncleaved detection probes, and nonspecific degradation products;

(iii) treating the assay mixture to exclude from the separation profile uncleaved detection probes and nonspecific degradation products; and (iv) separating and identifying the released molecular tags to determine each of the plurality of oligonucleotide labels.

A "helper probe" as used herein refers to a probe in a nucleic acid-based signal amplification technique that is required to create a structure that is necessary for nuclease activity to occur. Helper probes include primers, e.g. Gelfand (cited above) or Western et al. (cited above), "invader" or "pilot" probes, e.g. Brow et al. (cited above), "arm" regions of a complex, e.g. Hogan et al. (cited above), and the like. A "detection probe" as used herein is the probe that is cleaved by a nuclease to release a molecular tag in the present invention, e.g. the complement of an "arm" region (Hogan et al., cited above); a "taqman" probe, e.g. Gelfand (cited above); or the like. Pairs of helper probes and detection probes are operationally associated in an assay. Usually, such pairs of probes hybridize to an oligonucleotide label at adjacent sites, which may be contiguous regions, and the hybridization of both probes is necessary for a cleavage event to take place. For example, when a helper probe is a primer, it hybridizes or anneals to an oligonucleotide label in a complementary region after which it is recognized by a polymerase. The polymerase extends the primer and, if it has 5'→3' nuclease activity, it degrades any detection probe that may be adjacent and "downstream" of the primer. In other examples, the helper probe and detection probes may hybridize to the oligonucleotide label in immediately adjacent sites, e.g. Western (cited above), so that there is no intervening single stranded region between the probes. Usually, a pair of such probes hybridizes to an oligonucleotide label with a few hundred nucleotides of one another, e.g. 500 to 1000, and preferably, with a few tens of nucleotides of one another, e.g. 0 to 60. Preferably, a signal generation technique is employed that does not require temperature cycling, i.e. operates isothermally, using probe recycling to accumulate released molecular tags for separation.

B. Examples of Cleavage Structures (B1) In one embodiment of the method, the helper probe has a first segment complementary to a first region of the oligonucleotide label, and the detection probe has a first segment complementary to the oligonucleotide label at a region adjacent said first region, and a second segment complementary to a second segment of the helper probe, such that the helper probe and the detection probe form a recognition duplex upon hybridization to each other and to the oligonucleotide label.

Formation of a recognition duplex, or cleavage structure, in accordance with this embodiment is illustrated in FIG. 2A. Detectable signals corresponding to analyte are generated by the following steps: (1) providing for each oligonucleotide label 106 a helper probe 100 complementary to a first region 110' of the oligonucleotide label and a detection probe 102 complementary to the helper probe and to the oligonucleotide label at a second region 114' adjacent to said first region, such that the helper probe and the detection probe form a recognition duplex 112 upon hybridization to each other and to the oligonucleotide label, each detection probe having attached a molecular tag (designated "eTag" in the Figure) with a separation or detection characteristic distinct from those of other molecular tags, so that each molecular tag forms a distinguishable peak in a separation profile of the tags; (2) combining under hybridization conditions the sample, the helper probes, and the detection probes to form an assay mixture such that recognition duplexes are formed; (3) cleaving the recognition duplexes at a cleavage site so that molecular tags are released; and (4) separating and identifying the released molecular tags to detect each of the plurality of oligonucleotide labels.

The helper probe 100 and detection probe 102 of each pair of such probes each possesses a region (110 and 114, respectively) that hybridizes to an oligonucleotide label and a region (108 and 108', respectively) that hybridizes to the other probe of the pair to form a recognition duplex, as shown in FIG. 2A. The probe regions hybridizing to one another or to the oligonucleotide label have nucleotide sequences that are complementary to one another. This complementarity need not result in a perfectly matched duplex. Indeed, as described below, in some cases, the recognition duplex intentionally contains a mismatched basepair which serves as a specific recognition structure for a cleavage agent. These regions of the probe pairs are designed such that the melting temperature of the recognition duplex in the absence of an oligonucleotide label is less than the operating temperature of the assay, preferably 4° C. less (more preferably 7–10° C. less) than the operating temperature, so that little or no hybridization of the regions forming the recognition duplex occurs in the absence of oligonucleotide label. When the operating temperature of an assay reaction is about 60° C., the preferred length of exactly complementary regions forming a recognition duplex is approximately 8 to 20 contiguous bases (dependent on base composition and sequence). Other reaction conditions would potentially lead to a different size range; this is readily determined empirically.

Upon contacting the probes with a solution containing a target nucleic acid, the probe regions of the two probe oligonucleotides hybridize to their respective target regions on the oligonucleotide label. These regions are typically adjacent to one another, as shown in FIG. 2A, although they do not have to be immediately adjacent. The mutually complementary regions of the two probe strands are thus constrained to be in close proximity to one another, increasing the stability of the associated duplex.

The regions of the probes that are complementary to a target oligonucleotide label can be designed in a variety of manners. For example, these regions can be designed similarly to the regions forming the recognition duplex in that the Tm of either region alone (i.e., one probe strand plus the target strand) is below the operating temperature, but is above the operating temperature when both probe strands and the target strand are present and the regions forming the recognition duplex are hybridized. They can also be designed such that the Tm's of the probe regions are both above the operating temperature, or they can be designed such that one Tm is above and one Tm is below the operating temperature. Whatever design is chosen, the requirement that the regions making up the recognition duplex form a stable duplex only in the presence of target (oligonucleotide label) must be met. The regions of the probes complementary to target oligonucleotide labels are preferably between 8 and 50 nucleotides in length, more preferably between 8 and 30 nucleotides in length. These regions can be longer, but most applications do not require this additional length, and synthesis of these longer oligonucleotides is more costly and time consuming than the shorter oligonucleotides.

As illustrated in FIG. 2A, a stable multi-strand complex is formed under assay conditions only in the presence of all three members: helper probe (100), detection probe (102), and oligonucleotide label (106). Detection probe (102) is designed so that alone it is unable to form a stable duplex with oligonucleotide label (106) under predetermined assay conditions. When such a complex (107) is formed, the complementary regions of the helper probe (108) and detection probe (108') hybridize to form a recognition duplex (112). In order to form a three-strand complex, both helper probe (100) and detection probe (102) have complementary regions (110) and (114) to sites (110') and (114'), respectively, of oligonucleotide label (106). Oligonucleotide label (106) may be either a single stranded DNA or a single stranded RNA, such as a messenger RNA (mRNA).

As illustrated in FIG. 1B, in the operation of an assay of the invention, a plurality of pairs (120) of helper probes and detection probes are combined with a corresponding plurality of oligonucleotide labels (122) under conditions that permit the formation of recognition duplexes (124) among the pairs whenever their corresponding oligonucleotide label is present. Recognition duplexes (124) are recognized by a cleavage agent that specifically cleaves (126) only nucleic acids that are present in duplex form, to release a fragment of the detection probe which comprises a molecular tag. Thus, single stranded nucleic acids, including unbound helper probe, unbound detection probe, and oligonucleotide labels are not cleaved or modified. Preferably, the cleavage agent is a nuclease whose substrate is, or includes, a duplex structure comprising two DNA strands, two RNA strands, or a DNA strand and an RNA strand. After cleavage of the detection probe, the recognition duplex de-stabilizes because fewer nucleotides are based-paired in the duplex, which, in turn, leads to the destabilization (128) of the entire three-strand complex. Under the assay conditions (which include providing the detection probe in substantial excess concentration over the oligonucleotide labels), uncleaved detection probe participates in successive cycles (130) of complex formation and cleavage, until a desired detectable quantity of released molecular tags accumulate in the assay mixture.

After the assay reaction is complete, released molecular tags are separated and identified (132) using conventional separation techniques, e.g. capillary electrophoresis, microbore chromatography, or the like.

(B2.) In another embodiment of the method, the detection probe has a hybridizing region that hybridizes to the oligonucleotide label, and a 5' region, containing the molecular tag, that does not hybridize to the oligonucleotide label; and the helper probe hybridizes with the oligonucleotide label at a region 3' of the hybridizing region of the detection probe. An example of this method of forming a cleavage structure is described in U.S. Pat. No. 6,121,001 (Western et al.). Accordingly, an oligonucleotide detection probe is reversibly hybridized with an oligonucleotide label sequence under isothermal conditions. The detection probe includes a region of about 10 to 40 nucleotides that hybridizes with the target oligonucleotide label sequence, and may include a 3'-sequence that does not hybridize with the target sequence. The duplex formed thereby is cleaved at the 5'-end of the detection probe, by a 5'-nuclease, to provide a cleaved fragment, preferably 1–3 nucleotides in length, that includes a molecular tag. In one embodiment, the probe has a 5' region, typically 1 to 20 nucleotides in length, that does not hybridize to the target sequence, and the molecular tag is within this region. Cleavage by the nuclease typically occurs within 5 nucleotides of the junction of the non-hybridized sequence with the hybridized sequence of the detection probe.

The isothermal conditions are chosen such that equilibrium exists between oligonucleotide label-detection probe duplex and the various single stranded species in the assay mixture; i.e. the oligonucleotide label, the intact detection probe, and the fragments of the cleaved detection probe. The intact probe is preferably employed in large excess relative to the amount of oligonucleotide label. Under these conditions, repeated hybridization and cleavage of probe occurs. Preferably, the components are contacted with the nuclease for a period of time effective to produce at least a 100-fold molar excess of cleavage product relative to the oligonucleotide label.

The cleavage structure may also include a second, typically non-labeled oligonucleotide probe (helper probe), which hybridizes with the oligonucleotide label at a region 3' of and adjacent to the hybridized 5' end of the detection probe. The helper probe is preferably longer than the hybridized region of the detection probe, and has a melting temperature, when hybridized to the target oligonucleotide label sequence, which is preferably at least as high, and more preferably at least 5° C. higher than the melting temperature of the detection probe hybridized to the target oligonucleotide label. The presence of the helper probe in the cleavage structure enhances cleavage of the detector probe.

The 5'-nuclease used for cleavage can be any sequence-independent deoxyribonuclease enzyme that catalyzes the cleavage of an oligonucleotide into fragments only when at least a portion of the oligonucleotide is hybridized to the target oligonucleotide label sequence. The enzyme selectively cleaves the oligonucleotide near the 5'-terminus of the hybridized portion, within 5 nucleotides thereof, preferably within 1 to 2 nucleotides thereof, and does not cleave the unhybridized oligonucleotide probe(s) or the target oligonucleotide sequence. Such enzymes include both 5'-exonucleases and 5'-endonucleases but exclude ribonucleases such as RNAse H and restriction enzymes. Useful examples include thermally stable nucleotide polymerases having 5'-exonuclease activity such as Taq DNA polymerase (e.g. AmpliTaq™ from Perkin-Elmer Corporation, Norwalk, N.J.), Thermalase Tbr™ DNA polymerase (Amresco, Solon, Ohio), Ultra Therm™ DNA polymerase (Bio/Can Scientific, Ontario, Canada), Replitherm™ DNA polymerase (Epicentre, Madison, Wis.), Tfl™ DNA polymerase (Epicentre), Panozyme™ DNA polymerase (Panorama Research, Mountain View, Calif.), Tth™ DNA polymerase (Epicentre), rBst™ DNA polymerase (Epicentre), and Heat Tuff™ DNA polymerase (Clontech, Palo Alto, Calif.).

(B3.) In a further embodiment of a cleavage structure, such as illustrated in FIG. 3A, the helper probe is complementary to a first region of the oligonucleotide, and the detection probe is complementary to a second region of the oligonucleotide which overlaps the first region, such that a 3' nucleotide of the helper probe and an internal nucleotide of the detection probe are complementary to the same position of the oligonucleotide. As shown in FIG. 3A, hybridization of the helper probe 28 and detection probe 30 to the template oligonucleotide 32 thus produces a triplex, or cleavage structure, in which a strand 34 of the detection probe 30 immediately adjacent the internal nucleotide remains unhybridized. Such cleavage structures are described, for example, in U.S. Pat. No. 6,001,567. Linked to strand 34 is the electrophoretic tag 36.

With further reference to FIG. 1C, the helper probe(s), detection probe(s) and nuclease are added (38, 40) to the analyte complexes (bound ligand-oligonucleotide conjugates) under hybridization conditions, such that the helper probe, detection probe and oligonucleotide label form a cleavage structure which is recognized by the nuclease, and such that the nuclease cleaves and releases the electrophoretic tag. In one embodiment, at least the 3' portion of the helper probe anneals to the template oligonucleotide, and at least the 5' portion of the detection probe also anneals to the template oligonucleotide, to from a cleavage structure, such as illustrated at 42 in FIG. 1C.

In FIG. 1C, detection probes bearing molecular tags labeled 1–4 are bound to antibody-oligonucleotide conjugates 16, 18, 20, and 22, respectively, while a detection probe bearing an molecular tag labeled etag5, which corresponds to antibody-oligonucleotide conjugate 24, remains unbound (44).

The helper probes, detection probes, and nuclease may also be added simultaneously. The nuclease is an enzyme that recognizes the cleavage structure and cleaves the detection probe, generally at the site of displacement from the oligonucleotide label, to release the molecular tag. Such enzymes include those having 5' endonuclease activity, as described further below.

As described in Murante et al., 1995, such cleavage can also occur when the helper probe anneals to the template with a one-base mismatched overhang at the 3' terminus. Accordingly, "a 3' nucleotide of the helper probe" can refer to the terminal or the penultimate nucleotide at the 3' end of the helper probe.

Preferably, the assay is carried out under conditions such that multiple probe cleavages take place on a single analyte complex, as shown in FIG. 3B. The detection probe, and optionally the helper probe, are present in excess, and the components are combined under conditions such that cleaved detection probe (46) is repeatedly displaced from the oligonucleotide label by additional full length detection probe (30), which is cleaved in turn. This process, in which the oligonucleotide label 32 and helper probe 28 can be regarded as cofactors for the nuclease, produces a large number of released tags (48) for every analyte complex 26.

C. Illustrations Using Specific Enzymes

In FIG. 4A, an embodiment of the invention using hOGG1 protein as a cleavage agent is illustrated. Helper probe (202) and detection probe (200) are combined under assay conditions that permit the formation of a stable complex (207) with target oligonucleotide label (204). Preferably, detection probe (200) of the invention is defined by the formula:

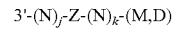

$$3'\text{-}(N)_j\text{-}Z\text{-}(N)_k\text{-}(M,D)$$

where N is a nucleotide, j is an integer in the range of from 8 to 40, k is an integer in the range of from 1 to 3; Z is a modified nucleoside recognized by hOGG1 protein when in a recognition duplex; preferably, Z is 7,8-dihydro-8-oxo-2'-deoxyguanosine ("8-oxo-G"), formamidopyrimidine guanosine, or methylformamidopyrimidine guanosine; and (M,D) is a molecular tag as described further below. Preferably, at least one nucleotide in the moiety "3'-(N)_j" has a capture ligand attached to exclude uncleaved probe or non-tag fragments (210) from separation. Preferably, the capture ligand is biotin and the capture agent is streptavidin.

Complex (207) includes a recognition duplex (205) which includes a deoxycytosine:8-oxo-G basepair. Recognition duplex (205) is recognized by hOGG1 protein, and 8-oxo-G is excised (209), releasing a molecular tag (208) and cleavage fragment (210) having a 5' phosphate. Preferably, molecular tag (208) is defined by the formula:

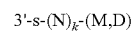

$$3'\text{-s-}(N)_k\text{-}(M,D)$$

where "s" is an open ring sugar comprising five carbon atoms and two oxygen atoms, N is a nucleotide, k is an integer in the range of from 1 to 3, and (M,D) is a molecular tag comprising a mobility modifying group and a detectable label, as described further below. Preferably, the structure "-(M,D)" is attached to $(N)_k$ by a phosphate linker. Detection probes (200) of this embodiment may be synthesized using conventional phosphoramidite chemistry, where in particular 8-oxo-G phosphoramidite monomers are made as disclosed, e.g. by Koizume et al., *Nucleosides and Nucleotides* 13: 1517–1534 (1994) or Kohda et al., *Chem. Res. Toxicol.* 9: 1278–1284 (1996).

The cleavage or exchange of detection probe (200) causes the de-stabilization (212) of complex (207) so that target oligonucleotide label (204) becomes available to re-cycle (214) in another complex (207). Preferably, as taught by Western et al., U.S. Pat. No. 6,121,001, providing electrophoretic probe (200) in high molar excess of the target or helper probe (202) enhances re-cycling (214). The reaction continues (215) for a time until a sufficient quantity of released molecular tags are accumulated. The reaction time is determined empirically and depend of parameters that would be readily manipulated by one of ordinary skill in the art, such as reaction temperature, nuclease concentration, helper probe concentration, detection probe concentration, salt concentration, probe lengths and compositions, and the like.

When the reaction is ended, molecular tags are separated from the assay mixture and from one another for detection. The separation step preferably includes a step for excluding material that may interfere with the separation or detection of the released molecular tags. Examples of such procedures include (1) attaching a quencher to detection probes so that a fluorescent label of uncleaved probes is undetectable if it is separated with released molecular tags, (2) attaching a capture ligand to detection probes, preferably on the probe opposite the site of cleavage, which capture ligand is combined with a reciprocal binding agent or receptor that imparts a charge to the bound probe or fragment that is opposite the charge of a released molecular tag (for electrophoretic separation), or (3) filtering larger molecular weight compounds or particulate matter to exclude it from being separated.

After the reaction is concluded, molecular tags (208) are separated and identified (216), as described further below.

Figure 4B:
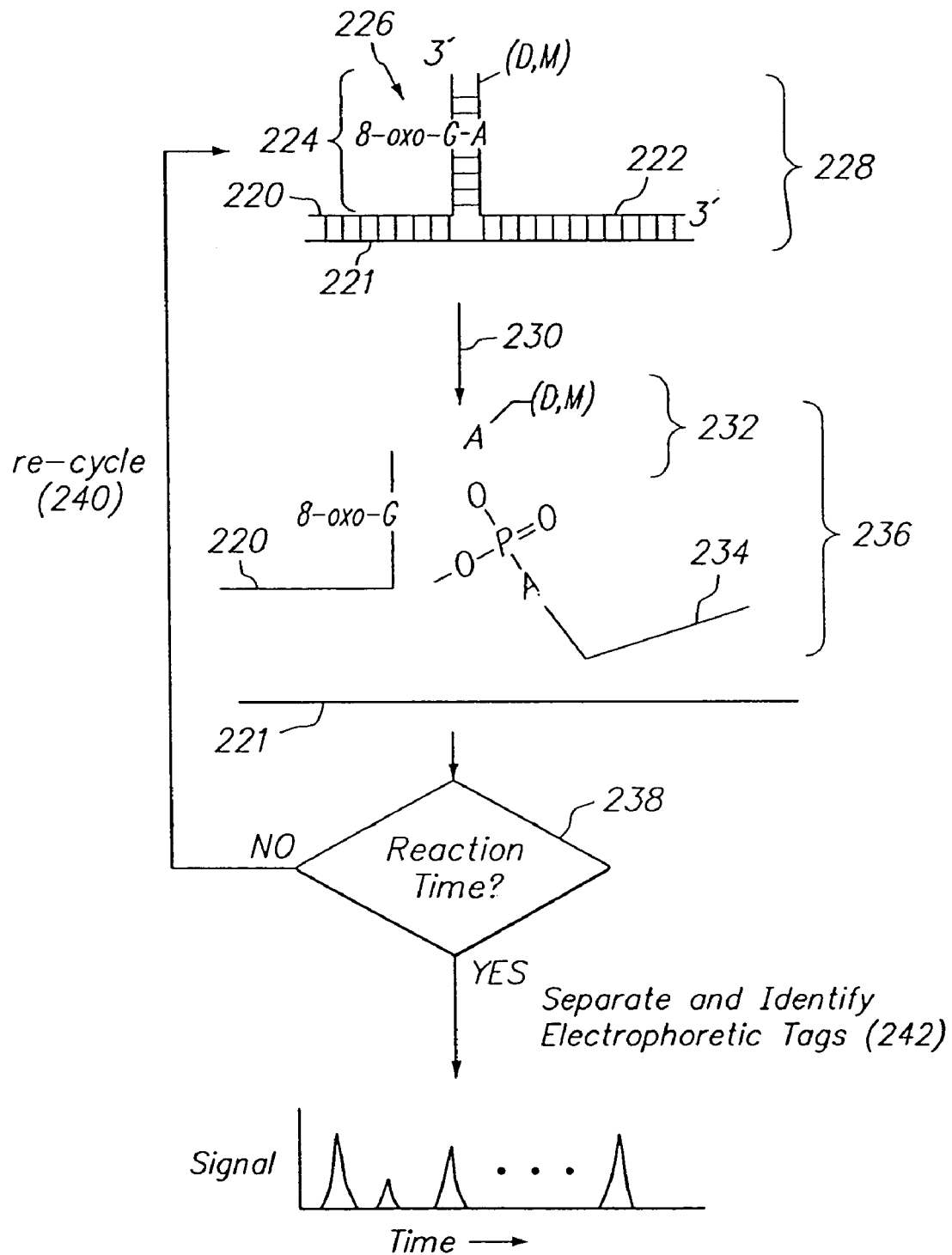
FIG. 4B illustrates an example of an assay in accordance with the invention in which the cleavage agent is MutY protein.

In FIG. 4B, an embodiment of the invention using MutY protein as a cleavage agent is illustrated. Helper probe (220) and detection probe (222) are combined under assay conditions that permit the formation of a stable complex (228) with target oligonucleotide label (221). Preferably, detection probe (222) of the invention is defined by the formula:

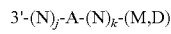

3'-$(N)_j$-A-$(N)_k$-(M,D)

where N is a nucleotide, j is an integer in the range of from 8 to 40, k is an integer in the range of from 1 to 3, and (M,D) is as described above. As above, preferably, at least one nucleotide in the moiety "3'-$(N)_j$" has a capture ligand attached to exclude uncleaved probe or non-tag fragments (234) from separation. Preferably, the capture ligand is biotin and the capture agent is streptavidin.

Helper probe (220) of the invention is defined by the formula:

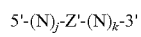

5'-$(N)_j$-Z'-$(N)_k$-3' where N, k, and j are defined as above, and Z' (226) is a modified nucleoside recognized by mutY protein when base paired with deoxyadenosine in a recognition duplex; preferably, Z' is 7,8-dihydro-8-oxo-2'-deoxyguanosine ("8-oxo-G").

Complex (228) includes a recognition duplex (224) which includes a deoxyadenosine:8-oxo-G basepair. Recognition duplex (224) is recognized by mutY protein, and the deoxyadenosine base paired with the 8-oxo-G is excised, releasing molecular tag (232) and cleavage fragment (234) having a 5'-phosphate. Preferably, molecular tag (232) of the invention is defined by the formula:

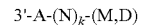

3'-A-$(N)_k$-(M,D)

where A is deoxyadenosine, N is a nucleotide, k is an integer in the range of from 1 to 3, and (M,D) is a molecular tag comprising a mobility modifying group and a detectable label, as described further below. Preferably, the structure "-(M,D)" is attached to $(N)_k$ by a phosphate linker.

Helper probe (220) of this embodiment may be synthesized using conventional phosphoramidite chemistry. The cleavage or exchange of detection probe (222) causes the de-stabilization (230) of complex (228) so that target oligonucleotide label (221) becomes available to re-cycle (240) in another complex (228). Again, as taught by Western et al., U.S. Pat. No. 6,121,001, providing electrophoretic probe (222) in high molar excess of the target or helper probe (220) enhances re-cycling (240). The reaction continues (238) for a time until a sufficient quantity of released molecular tags are accumulated. The reaction time is determined empirically and depends on parameters that are readily manipulated by one of ordinary skill in the art, such as reaction temperature, nuclease concentration, helper probe concentration, detection probe concentration, salt concentration, probe lengths and compositions, and the like. When the reaction is ended, molecular tags are separated (242) from the assay mixture and from one another for detection. Optionally, as described above, additional steps may be taken to exclude interfering material from separation of the released molecular tags.

IV. Multiple-Event Binding

Figure 5:
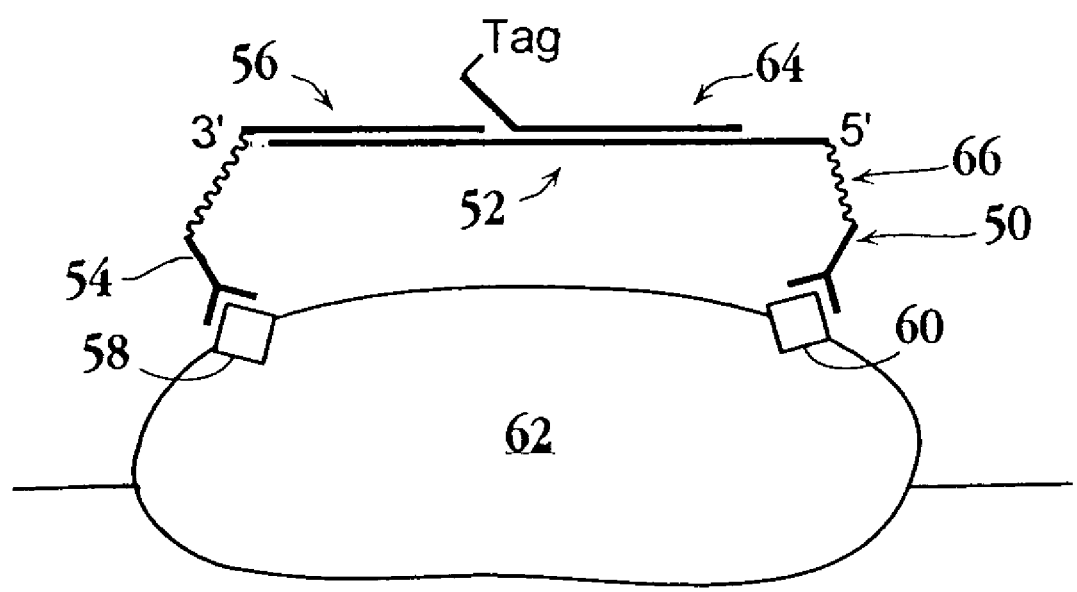
FIG. 5 illustrates an analyte complex with bound detection probe, as formed in a multiple binding event assay format.

The invention also provides methods for targeting coupled or multimeric binding sites on an analyte. For example, a cell surface receptor may include multiple binding sites specific for different antibodies. Accordingly, specific pairs of ligand-oligonucleotide conjugates are employed, one of which is shown, as part of an analyte complex, in FIG. 5. The first binding agent (50) is linked to a template oligonucleotide label (52), as described above, while the second binding agent (54) is linked to a primer or helper oligonucleotide probe, (56). As shown in the Figure, simultaneous binding of the ligands to their respective binding sites (58, 60) on the target (62) allows the template oligonucleotide and the primer to become hybridized, such that addition of a detection probe (64) forms a cleavage structure. By requiring both binding probes to be present at different binding sites on the analyte, the sensitivity of the assay for the analyte is increased.

Preferably, in each of the two conjugates, the binding agent and oligonucleotide are joined by a flexible linking group (66). The proximity required between the ligands to form the cleavage structure will determine the appropriate length of the linking group. A typical linking group, for example, consists of a PEG (polyethylene glycol) chain having about 2–50, more preferably about 5–25, ethylene oxide subunits, or a similar length chain comprising different linkages, connecting the ligand, such as an antibody, to the oligonucleotide. Such conjugates can be prepared in accordance with standard conjugation methods employed for biomolecules, as described further below.

V. Analysis of Tag Mixtures

Following cleavage of the tags, the released tags are separated, if necessary, and analyzed, e.g. by chromatographic separation, mass spectrometry, or, preferably, by electrophoretic separation. If other assay components or reagents, such as uncleaved detection probes or partially degraded detection probes, should interfere with electrophoretic analysis, it may be necessary to separate the released tags from the assay solution. Such separation can be accomplished by, for example, selective quenching of signal generation of uncleaved detection probes, isolation of tags via affinity chromatography (e.g. Ensing et al., Eur. pat. publ. 0671626 A1), ion exchange, liquid chromatography, initial electrophoretic separation, etc., or cleavage of unwanted components. In the latter case, cleavage may result in a change in charge, hydrophobicity, molecular weight, or like physical characteristics that permit the undesired components to be excluded.

Separation can also be accomplished using capture ligands, such as biotin or other affinity ligands, and capture agents, such as avidin, streptavidin, an antibody, a receptor, or a functional fragment thereof, having specific binding activity to the capture ligand. A tagged probe, or a target-binding moiety of a tagged probe, can contain a capture ligand having specific binding activity for a capture agent. For example, the target-binding moiety of a tagged probe can be biotinylated or attached to an affinity ligand using methods well known in the art. After the tag reporter is cleaved from the tagged probe, the remaining part of the tagged probe with the target-binding moiety and biotin can be removed by, for example, streptavidin agarose beads. A capture ligand and capture agent can also be used to add mass to the remaining part of the tagged probe such that it can be excluded from the mass range of the tag reporters separated by chromatography.

Figure 1D:
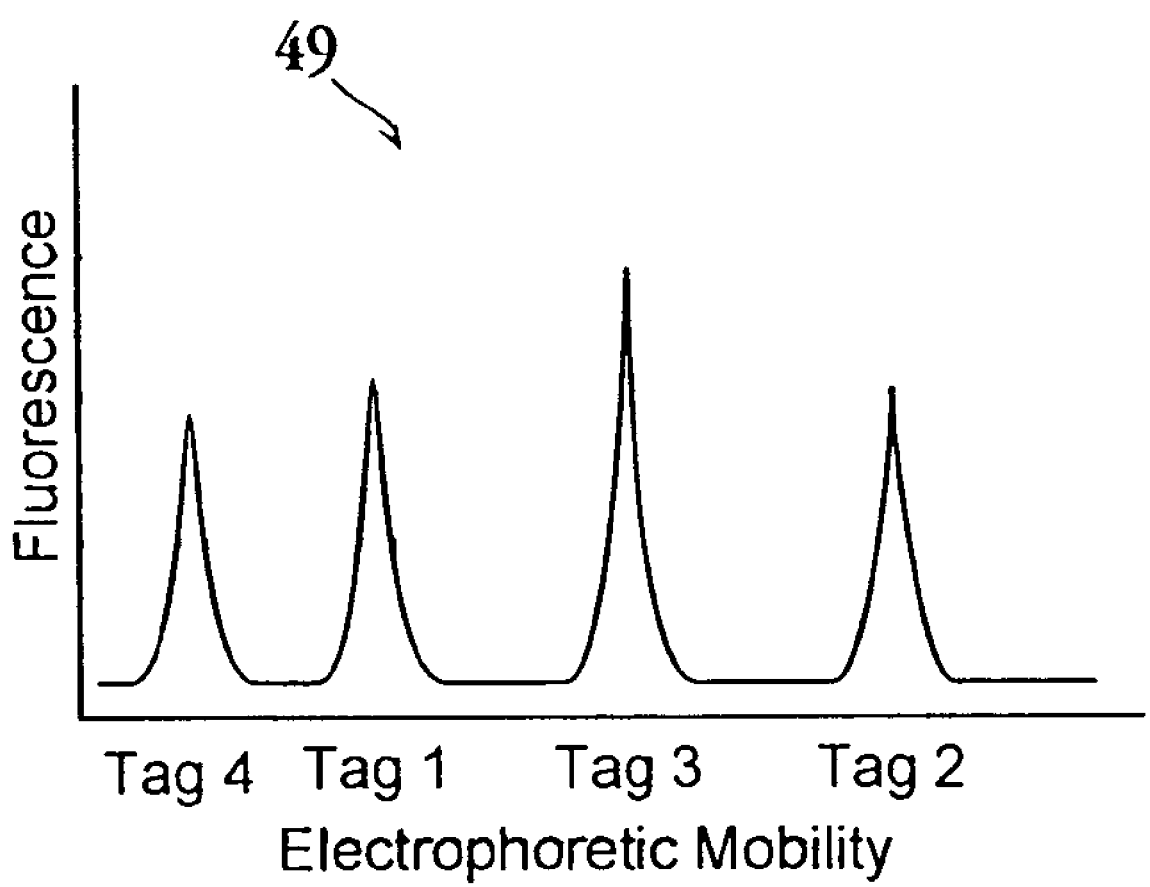
Figure 2B:
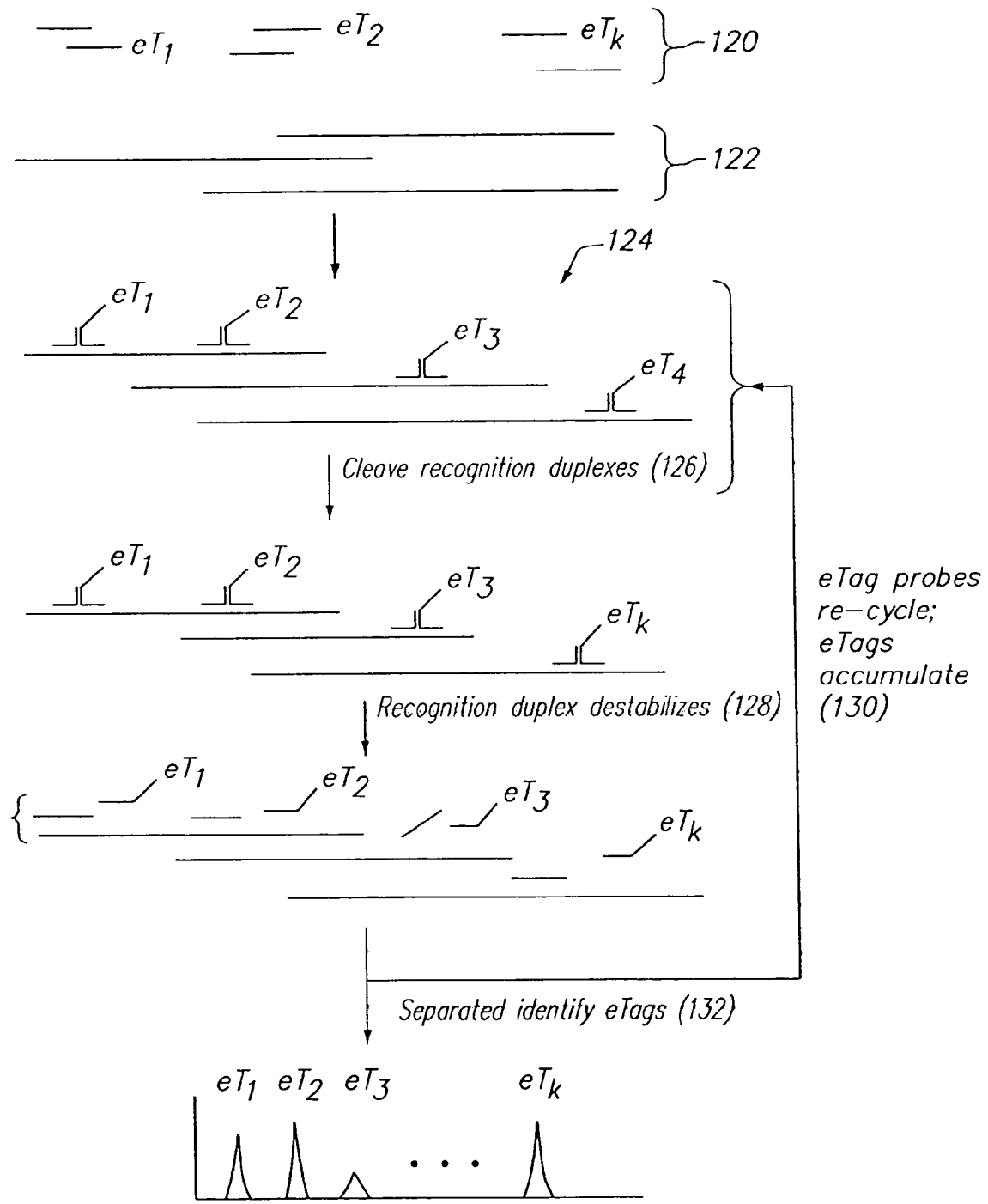
FIG. 2B illustrates the operation of one embodiment of the invention for detecting a plurality of target oligonucleotide labels.

The separated peaks are detected, e.g. by fluorescence emission detection of fluorescent labels in the tags. Because the separation characteristics of the molecular tags released from the respective probes are known, the multiplex data output, e.g. an electropherogram, such as shown schematically at 49 in FIG. 1D and in FIGS. 2B and 4B, can be used to identify the ligand-oligonucleotide conjugates which bind to analytes in the sample. As can be seen, "Tag 5" is absent in FIG. 1D, since its corresponding ligand-oligonucleotide complex (binding composition) did not bind to any target in the sample (as shown in FIGS. 1A–C). Intensity of peaks can also be used to determine the relative amount of different analytes in the sample, based on the ligands which bound to the analytes.

Preferably, the labels employed in the molecular tags are such that peak height or area of different tags can be directly correlated to the number of tags detected. For example, a set of probes may employ tags having the same label and different mobility modifying groups, as discussed further below.

A known amount of a "standard" molecular tag may be added to the test assay to provide a standard for calibrating the mobility and peak characteristics of the released tag(s). The measured peak height or area under the curve (AUC) of the standard molecular tag, relative to the known amount of standard molecular tag added, can be used to calculate the amount of test and control molecular tags from the measured peak heights or AUC in the electropherogram.

Once a solution of cleaved e-tag reporters is prepared and is free of any interfering components, the composition of the solution is analyzed. The released tags from an assay are preferably separated on a single separation medium or format, meaning that a sample mixture containing the combined tags is applied to a single separation medium, such as electrophoretic separation medium, a chromatography medium, or a mass spectroscopy medium, and all of the sample product/substrates components are separated on that medium.

A preferred separation medium is an electrophoretic medium. The analysis may employ capillary electrophoresis devices, microfluidic devices or other devices that can separate a plurality of compounds electrophoretically, providing resolved bands of the individual e-tag reporters. A preferred separation device is a microfluidics device of the type described above for separating charged components across a separation channel, according to well-known methods. The electrophoretic device is generally connected to a data processor for receiving and processing data from the device, as well as operating the electrophoretic device. Electrophoretic separation and band resolution of a plurality of probes and substrates is readily accomplished by this method.

Conveniently, an aliquot, generally not more than about 5 μl, is transferred to the sample reservoir of a microfluidics device or capillary electrophoretic device, either directly through electrophoretic or pneumatic injection into an integrated system or by syringe, capillary or the like. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876. The conditions under which the separation is performed are conventional and will vary with the nature of the products. Longer times will be required for products that have similar mobilities under the conditions of the electrophoresis.

Figure 6:
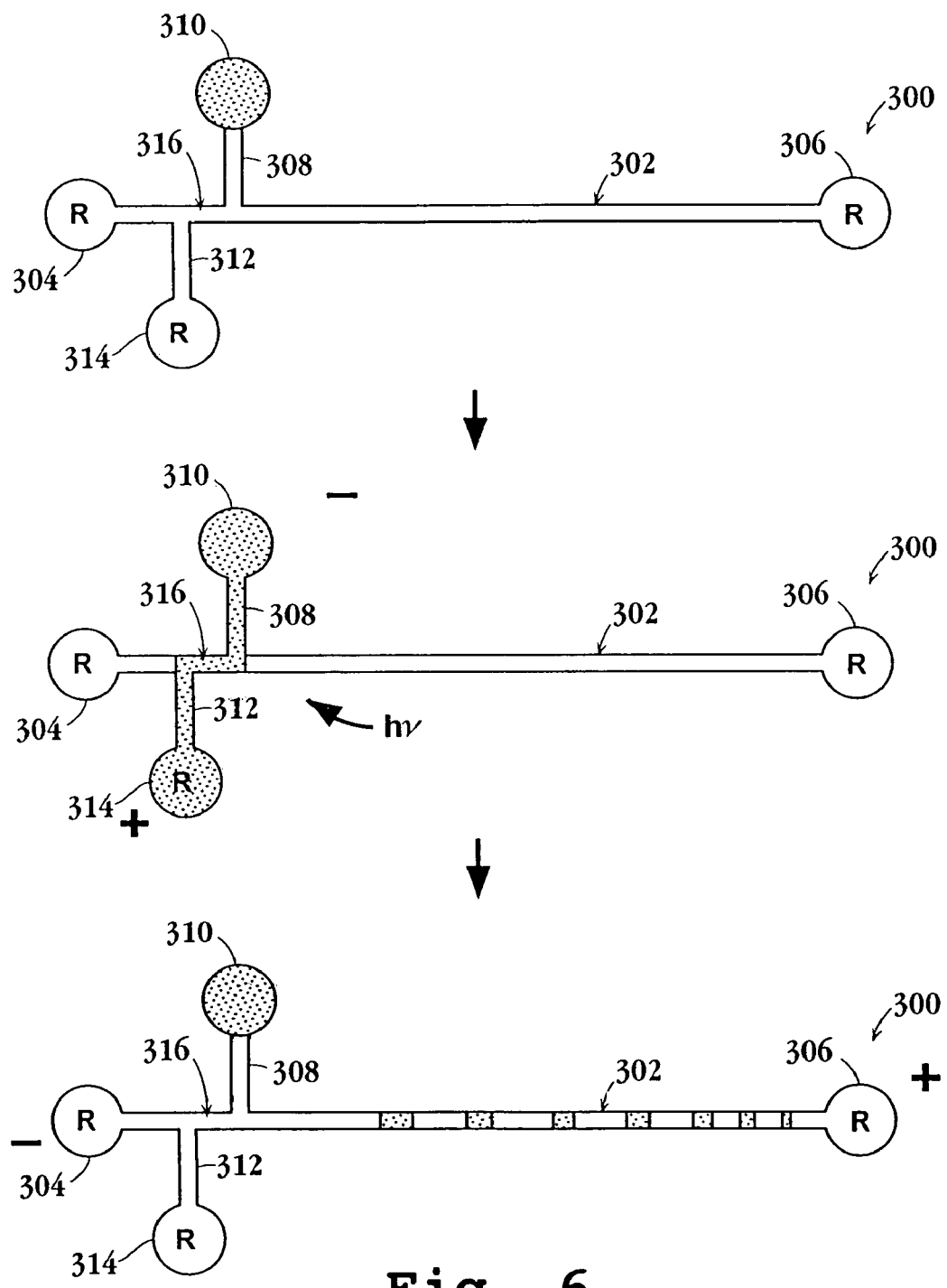
FIG. 6 shows steps in practicing the methods of the invention using a microfluidics/capillary electrophoresis (CE) device.

By way of illustration, FIG. 6 shows a microchannel network 300 in a microfluidics device of the type detailed in the application noted above, for sample loading and electrophoretic separation of a sample of probes and tags produced in the assay above. Briefly, the network includes a main separation channel 302 terminating at upstream and downstream reservoirs 304, 306, respectively. The main channel is intersected at offset axial positions by a side channel 308 that terminates at a reservoir 310, and a side channel 312 that terminates at a reservoir 314. The offset between the two side channel forms a sample loading zone 316 within the main channel.

In operation, the assay mixture from above is placed in sample reservoir 310, illustrated in FIG. 6. As noted, the assay mixture contains one or more target cells with surface-bound detection probe, one or more test ligands, and optionally, a molecular tag standard. The assay reaction, involving initial binding of binding compositions to target cell(s), followed by cleavage of detection probe, may be carried out in sample reservoir 310, or alternatively, the assay reactions can be carried out in another reaction vessel, with the reacted sample components the added to the sample reservoir.

To load released molecular tags into the sample-loading zone, an electric field is applied across reservoirs 310, 314, as indicated in the Figure, drawing negatively charged released probes from reservoir 310 into loading zone 316, while uncharged or positively charged sample components remain in the sample reservoir. The released tags in the loading zone can now be separated by conventional capillary electrophoresis, by applying an electric filed across reservoirs 304, 306, as indicated in the Figure.

From the resulting electrophoretic pattern, the tags, and corresponding cell types labeled by the tags, can be identified. This is typically done by placing a fluorescence detector near the downstream end of the separation channel, and constructing a electropherogram of the separated molecular tag components, first to determine the separation characteristic (in this case, electrophoretic mobility) as above, and secondly, to measure signal intensity, e.g., peak height or peak area, as a measure of the relative amount of tag associated with each probe. Methods for detecting and quantifying levels of a detectable probe are well known. In one preferred method, the tags are fluorescent labeled. A standard fluorescence-emission source is directed against a detection zone in a downstream portion of the separation medium, and fluorescence emission of the zone is measured by a standard light detector. The signal height or area recorded provides a measure of product and substrate concentration in the sample.

Addition of a known quantity of a control fluorophore to each sample before separation of the e-tag reporters by electrophoresis allows conversion of relative fluorescent signals into absolute quantities. Any fluorophore that does not interfere with detection of the e-tag reporter signals can be used for normalizing the fluorescent signal. The control signal will preferably have an electrophoretic mobility that is different from that of any of the e-tag reporters in the sample, and may have the same or a different emission wavelength. Exemplary control fluorescent molecules include ROX, FAM, and fluorescein.

With the above detection information, it is now possible to assign each detected tag to a particular binding composition, and to compare the relative levels of each detected tag, as a measure of binding of that binding composition to the cell.

VI. Assay Components

A. Antibodies

In most instances, the binding agent component of the ligand-oligonucleotide conjugate is a protein, typically an antibody. In general, an antibody is an immunoglobulin (a class of globular protein) present in the serum of an animal that is produced by lymphocytes (plasma cells) in response to the presence of an antigen. An antibody specifically binds to, and is thereby defined as complementary with, a particular spatial and polar organization of another molecule. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular analyte is maintained. Such conjugates may include, for example, antibodies linked to biotin for separation purposes.

Antibodies can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies.

A "monoclonal antibody" (MAB) is an immunoglobulin produced by a single clone of lymphocytes, i.e. the progeny of a single B cell, which recognizes only a single epitope on an antigen. MAB can be produced experimentally from hybridoma cells, e.g. according to the standard techniques of Köhler and Milstein, *Nature* 265:495–497, 1975. Reviews of monoclonal antibody techniques are found in *Lymphocyte Hybridomas*, ed. Melchers et al., Springer-Verlag (New York 1978); *Nature* 266: 495 (1977); *Science* 208: 692(1980), and *Methods of Enzymology* 73 (Part B): 3–46(1981).

In one method of producing MAB targeted to a specific receptor, cells carrying the particular receptor, such as a cancer-specific receptor, are injected into a mouse, thereby inducing the mouse's antibody producing cells (B lymphocytes) to produce antibodies against all of the receptors on the cell surface. These B cells are extracted and fused to immortalized (endlessly replicating) cells in culture to create hybridomas. Modifications of this standard method have been developed which create "humanized" MAB. Thus, in one embodiment of the invention, test monoclonal antibodies are produced by antibody-secreting hybridoma cells, and the test antibodies added to the target cells are harvested from a culture of the hybridoma cells.

MAB can also be produced by a library of phage engineered to display a library of immunoglobulin fragments as binding moieties on the phage surface. Briefly, to produce a phage display antibody library, cDNAs of immunoglobulins isolated by PCR from immunized B lymphocytes (each cell of which makes antibodies against only one antigen) are inserted into the genome of filamentous phage or a phagemid vector which is introduced into *E. coli* host cells. As the phages replicate, antibodies encoded by the genes of the various B lymphocytes are expressed on their surfaces. The phage library is screened to identify those phage whose displayed proteins (antibodies) bind to a target.

In another approach for the preparation of antibodies, a sequence coding for antibody binding site(s) can be excised from chromosomal DNA and inserted into a cloning vector, which can be expressed in bacteria to produce recombinant proteins having the corresponding antibody binding sites. To facilitate extraction or purification of an expressed antibody from an expression system, a gene sequence encoding a defined affinity peptide tag (e.g. 6×His, HA, myc, etc.) can be inserted at the amino or carboxy-terminus of the immunoglobulin gene sequence.

Various conventional methods exist for isolation and purification of monoclonal antibodies from other proteins and other contaminants (see Köhler and Milstein, supra). In general, antibodies can be purified by known techniques such as chromatography, e.g., DEAE chromatography, ABx chromatography, and the like, filtration, and so forth.

MAB targeted to various analyte species, such as cell surface receptors, can also be obtained commercially from a wide range of suppliers, e.g. Zymed Laboratories, Inc., South San Francisco, Calif.; Pierce Biotechnology, Rockland, Ill.; Abcam, Cambridge Science Park, UK.

B. Molecular Tags

The detection probes of the invention may be described by the formula T-E, where T is an oligonucleotide and E is a molecular tag. At least one nucleotide of T may also include a capture ligand. Molecular tag(s) E may be attached to T at a variety of sites. For example, E may be attached to any nucleoside of T, to any inter-nucleosidic linkage of T, or to a 3'-hydroxyl or a 5'-hydroxyl. Where molecular tags are released by nuclease activity, the released molecular tag generally includes a nucleoside or one or more nucleotides along with a mobility modifying moiety (M) and detectable label (D). Accordingly, in one aspect, released molecular tags are described by the formula:

(D,M)-N where the moiety "(D,M)-" is as described above and N is a nucleoside, nucleotide, a base, a ribose, or the like. Usually, N is a nucleoside.

As described more fully below, one aspect of the invention is the set of molecular tags generated in an assay. Generally, a set of molecular tags may be selected from a group of molecules having a wide variety of structures. The primary criterion for constructing a set is that each molecular tag must be distinguishable from all the other molecular tags of the same set under a predetermined method of separation and detection, as described in Singh, U.S. Pat. No. 6,322,980; Singh, PCT publication WO 00/66607; and Singh et al., PCT publication WO 01/83502, which references are incorporated by reference. That is, each molecular tag of a set must have distinct detection and/or separation characteristics that allow it to be detected and quantified after separation with the other tags. Preferably, molecular tags are detected by fluorescence characteristics and are separated by electrophoresis; however, other liquid phase separation techniques, especially chromatography, may also be used. Molecular tags of a set may be selected empirically; however, as illustrated below, members of a set may also be assembled from molecular building blocks with predictable separation characteristics.

For further description of binding compositions and electrophoretic tags, and their use in multiplexed assays, see, for example, co-owned U.S. application Ser. No. 09/824,851, published on Dec. 13, 2001 as US Appn. Pubn. No. 20010051340, co-owned PCT Pubn. Nos. WO 2000/6607 and WO 2001/83502, and co-owned U.S. provisional application Ser. No. 60/399,056, each of which is hereby incorporated by reference.

The molecular tag, attached to the oligonucleotide probe and cleaved thereof during the assay, is a water soluble compound that is stable with respect to the conditions employed for cleavage and release and that includes a detection or reporter group. Otherwise, the tag may vary widely in size and structure. Preferably, the tag carries a charge at neutral pH and has a molecular weight in the range of from about 150 to about 10,000 daltons, more preferably, from about 150 to about 5000 daltons, and most preferably, from about 150 to 2500 daltons. Preferred structures are described more fully below. Preferably, the detection group generates an electrochemical, fluorescent, or chromogenic signal. Most preferably, the detection group generates a fluorescent signal.

Preferably, each of the plurality of molecular tags employed in a single multiplexed assay has either a unique charge-to-mass ratio and/or a unique optical property with respect to the other members of the plurality. Preferably, the optical property is a fluorescence property, such as emission spectrum, fluorescence lifetime, or the like. More preferably, the fluorescence property is an emission spectrum. For example, each molecular tag of a plurality of tags may have the same fluorescent emission properties, but will differ from the others by virtue of unique charge-to-mass ratios. On the other hand, two or more of the molecular tags of a plurality of tags may have identical charge-to-mass ratios, but they will have unique fluorescent properties, e.g. spectrally resolvable emission spectra, so that all the members of the plurality are distinguishable by the combination of electrophoretic separation and fluorescence measurement.

Preferably, molecular tags in a plurality of tags are detected by electrophoretic separation and fluorescence. Preferably, molecular tags having substantially identical fluorescence properties have different electrophoretic mobilities so that distinct peaks in an electropherogram are formed under separation conditions. A measure of the distinctness, or lack of overlap, of adjacent peaks is electrophoretic resolution, which can be defined, in one of many ways, as the distance between adjacent peak maximums divided by four times the larger of the two standard deviations of the peaks. Preferably, adjacent peaks have a resolution, according to this definition, of at least 1.0, more preferably at least 1.5, and most preferably at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including the signal detection system, the nature of the fluorescent moieties, the diffusion coefficients of the tags, the presence or absence of sieving matrices, nature of the electrophoretic apparatus, e.g. presence or absence of channels, length of separation channels, and the like.

Preferably, pluralities of molecular tags released in an assay (each of which may include a portion of the probe from which it was cleaved) are separable by a conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Preferably, in such a conventional apparatus, the electrophoretic mobilities of a plurality of molecular tags differ by at least one percent, and more preferably, by at least a percentage in the range of from 1 to 10 percent. Electrophoretic mobility is proportional to $q/M^{2/3}$, where q is the charge on the molecule and M is the mass of the molecule. Desirably, the difference in mobility under the conditions of the determination between the closest molecular tags will be at least about 0.001, usually 0.002, more usually at least about 0.01, and may be 0.02 or more.

A preferred structure of a molecular tag can be represented by (M,D), where M is a mobility-modifying moiety and D is a detection moiety. The notation "(M,D)" is used to indicate that the ordering of the M and D moieties may be such that either moiety can be adjacent to the point of linkage to the probe.

B1. Detection Moiety D

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al., U.S. Pat. No. 6,191,278; Lee et al., U.S. Pat. No. 6,372,907; Menchen et al., U.S. Pat. No. 6,096,723; Lee et al., U.S. Pat. No. 5,945,526; Lee et al., Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al., U.S. Pat. No. 2,153,059; Eckert et al., U.S. Pat. No. 2,242,572; Taing et al., International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative.

In another aspect, the detection moiety of (M,D) generates a fluorescent signal by an energy transfer mechanism. Preferably, in this aspect, D has the form "$D_1$-g-$D_2$" where $D_1$ and $D_2$ are acceptor-donor pairs of molecules, e.g. Wu et al., *Anal. Biochem.* 218:1–13 (1994), and g is a rigid linker that maintains $D_1$ and $D_2$ at a substantially constant distance. Guidance in selecting rigid linker, g, may be found in Wu et al. (cited above) and in U.S. Pat. Nos. 5,863,727; 5,800,996; 5,945,526; and 6,008,379. Either $D_1$ or $D_2$ may be the acceptor and the other the donor molecule in the pair. Exemplary energy transfer detection moieties for use with the invention are disclosed in Lee et al., U.S. Pat. No. 5,945,526; Lee et al., *Nucleic Acids Res.* 25:2816–2822 (1997); Taing et al., PCT Publication WO 02/30944; and like references. Preferably, rigid linker, g, is selected so that the distance between $D_1$ and $D_2$ is maintained at a substantially constant distance within the range of from 10–100 Angstroms. A wide variety of linking groups may be employed with the proviso that the linkage is stable to the presence of singlet oxygen. Preferably, $D_1$ and $D_2$ are selected from the set of fluorescein, rhodamine, rhodamine 6G, rhodamine 110, rhodamine X, tetramethylrhodamine, and halogenated derivatives thereof. More preferably, $D_1$ and $D_2$ are both fluorescein dyes.

In one aspect, g may be selected from any of $R_1$—$R_2$—$R_1$ and $R_1$—$R_2$—$C(=O)$—$X_1$—$R_3$, the latter being present in either orientation with respect to $D_1$ and $D_2$; where $X_1$ is O, S, or NH; $R_1$ is ($C_1$–$C_5$ alkyldiyl, $X_1$, $C(=O)$) such that the moieties in parentheses are arranged in any linear order; $R_2$ is a 5 to 6 membered ring selected from the group consisting of cyclopentene, cyclohexene, cyclopentadiene, cyclohexadiene, furan, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene; and $R_3$ is $C_1$–$C_5$ alkyldiyl. By "$C_1$–$C_5$ alkyldiyl" is meant an divalent alkyl group having one to five carbons, e.g. —$CH_2$—, —$(CH_2)_5$—, or —$CH(CH_3)CH_2CH_2$—.

As described above, each e-tag moiety typically contains a detectable label D. Alternatively, an e-tag moiety may contain a functionality allowing it to bind to a label D after reaction with a sample is complete. In some instances, the detectable label may be part of the reagent cleaving the cleavable bond L. In one embodiment, a plurality of different functionalities are used for different binding members, for reaction with a label, and the different labels have corresponding functionalities that react with one of the first functionalities. For example, where the first functionalities include thiols, carboxyl groups, aldehydes and olefins, the labels could include activated olefins, alcohols, amines and thiol groups, respectively. By employing removable protective groups for one or more of the functionalities, the protective groups may be removed stepwise and the labels added stepwise, to avoid cross-reactivity.

B2. Mobility Modifier M

M is generally a chemical group or moiety having a particular charge-to-mass ratio and thus a particular electrophoretic mobility in a defined electrophoretic system. In a set of n detection probes, each unique mobility modifier may be designated $M_j$, where j=1 to n, and n has a value as described above. That is, n is generally from 5 to 200, and more preferably, from 5 to 100, or 5 to 75, or from 5 to 50, or from 10 to 30.

The mobility-modifying moiety may be considered to include a mass-modifying region and/or a charge-modifying region or a single region that acts as both a mass- and charge-modifying region. In the probe sets utilized in the invention, the mobility-modifying moiety may have one or more of the following characteristics: (i) a unique charge-to-mass ratio due to variations in mass, but not charge; (ii) a unique charge-to-mass ratio due to changes in both mass and charge; and (iii) a unique charge-to-mass ratio of between about −0.0001 and about 0.5, usually, about −0.001 and about 0.1. As noted above, D is typically the same among a set or plurality of different detection probes, but may also differ among probe sets, contributing to the unique electrophoretic mobilities of the released molecular tag.

The size and composition of mobility-modifying moiety, M, can vary from a bond to about 100 atoms in a chain, usually not more than about 60 atoms, and more usually not more than about 30 atoms, where the atoms are preferably selected from carbon, oxygen, nitrogen, phosphorous, boron and sulfur. Generally, when other than a bond, the mobility-modifying moiety has from about 0 to about 40, more usually from about 0 to about 30, heteroatoms, which in addition to the heteroatoms indicated above may include halogen or another heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (including ammonium), phosphonium, sulfonium, oxonium, etc., where substituents are generally aliphatic of from about 1–6 carbon atoms, the total number of carbon atoms per heteroatom usually being less than about 12, preferably less than about 9. Other substituents may include hydroxyl groups, including phenolic groups, carboxyl groups, esters, amides, phosphates, and heterocycles. The charged mobility-modifying moieties generally have only negative or only positive charges, although one may have a combination of charges, particularly where a region to which the mobility-modifying moiety is attached is charged and the mobility-modifying moiety has the opposite charge.

In various embodiments, M may an oligomer, having monomers of the same or different chemical characteristics, e.g., nucleotides and amino acids. The mobility-modifying moieties may comprise a single type of monomer that provides the different functionalities for oligomerization and that carries a charge. Alternatively, two or more different monomers may be employed. Substituted diols may be used, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as organic dibasic acids, such as oxalic acid, malonic acid, succinic acid, maleic acid, fumaric acid, carbonic acid, etc. Instead of using esters, amides may be used, and amino acids or diamines and diacids may be employed. Alternatively, the hydroxyls or amines may be linked with alkylene or arylene groups.

Pluralities of molecular tags may include oligopeptides for providing the charge, particularly oligopeptides of from 2–6, usually 2–4 monomers, either positive charges, resulting from lysine, arginine and histidine, or negative charges, resulting from aspartic and glutamic acid. Unnatural or synthetic amino acids, such as such as taurine, phosphate substituted serine or threonine, S-α-succinylcysteine, can also be used, as well as co-oligomers of diamines and amino acids, etc.

In one aspect of the present invention, the charge-imparting moiety is conveniently composed primarily of amino acids but also may include thioacids and other carboxylic acids having from one to five carbon atoms. The charge imparting moiety may have from 1 to about 30, preferably 1 to about 20, more preferably, 1 to about 10 amino acids per moiety and may also comprise 1 to about 3 thioacids or other carboxylic acids. However, when used with an uncharged sub-region, the charged sub-region will generally have from 1 to about 4, frequently 1 to about 3 amino acids. Any amino acid, either naturally occurring and/or synthetic, may be employed.

The desired charge-to-mass ratio can be achieved by employing monomers that have substituents that provide charges, or which may be modified to provide charges. For example, the hydroxyl groups of serine or threonine may be modified with phosphate to provide negatively charged mobility-modifying moieties. With arginine, lysine and histidine, positively charged mobility-modifying moieties are provided. Oligomerization may be performed in conventional ways to provide the appropriately sized mobility-modifying moiety. The different mobility-modifying moieties may have different orders of oligomers, generally from 1 to 20 repeating units, more usually about 1 to 12, where a repeating unit may have from 1 to 2 different monomers. For the most part, oligomers are used with other than nucleic acid target-binding regions. The polyfunctionality of the monomeric units provides for functionalities at the termini that may be used for conjugation to other moieties, so that the available functionality for reaction may be converted to a different functionality. For example, a carboxyl group may be reacted with an aminoethylthiol, to provide an amide with a terminal thiol functionality for reaction with an activated olefin.

By using monomers that have about 1 to about 3 charges, a low number of monomers can be employed to provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $D^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids can be used with a diamine to form a polyamide, while the hydroxyl groups can be used to form esters, such as phosphate esters, or ethers such as the ether of glycolic acid, etc.

To vary mobility, various aliphatic groups of differing molecular weight may be employed, such as polymethylenes, polyoxyalkylenes, polyhaloaliphatic or aromatic groups, polyols, e.g., sugars, where the mobility will differ by at least about 0.01, more usually at least about 0.02 and more usually at least about 0.5. Methods of forming selected-length polyethylene oxide-containing chains are well known, see, e.g. Grossman et al., U.S. Pat. No. 5,777, 096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. Additionally, polypeptides of selected lengths and amino acid composition (i.e., containing naturally occurring or man-made amino acid residues), as homopolymers or mixed polymers may be used.

Various oligomers may be synthesized on a support or produced by cloning or expression in an appropriate host. Conveniently, polypeptides can be produced having only one cysteine or serine/threonine/tyrosine, aspartic/glutamic acid, or lysine/arginine/histidine, other than an end group, providing a unique functionality which may be differentially functionalized. By using protective groups, a side-chain functionality can be distinguished from a terminal amino acid functionality. Also, by appropriate design, one may provide for preferential reaction between the same functionalities present at different sites on the mobility-modifying moiety. Whether one uses synthesis or cloning for preparation of oligopeptides, is to a substantial degree dependent on the length of the mobility-modifying moiety.

(M,D) moieties can be conveniently constructed from one or more of the same or different common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary precursors that form amide bonds include Fmoc- or Boc-protected amino acid precursors, and derivatives thereof, e.g. as commercially available from AnaSpec, Inc. (San Jose, Calif.). Exemplary precursors that form phosphodiester bonds include, but are not limited to, dimethoxytrityl (DMT)-protected hexaethylene glycol phosphoramidite, 6-(4-monomethoxytritylamino)hexyl-(2-cyanoethyl)-(N,N-diisopropyl)-phosphoramidite, 12-(4-monomethoxytritylamino)dodecyl-(2-cyanoethyl)-(N,N-diisopropyl)-phosphoramidite, 2-[2-(4-monomethoxytrityl) aminoethoxy] ethyl-(2-cyanoethyl), N,N-diisopropyl)-phosphoramidite, (S-trityl-6-mercaptohexyl)-(2-cyanoethyl)-(N,N-diisopropyl)-phosphoramidite, 5'-fluorescein phosphoramidite, 5'-hexachloro fluorescein phosphoramidite, 5'-tetrachloro fluorescein phosphoramidite, 9-O-dimethoxytrityl-triethylene glycol, 1-[(2-cyanoethyl)-(N,N-diisopropyl)]-phosphoramidite, 3-(4,4'-dimethoxytrityloxy)propyl-1-[(2-cyanoethyl)-(N,N-diisopropyl)]-phosphoramidite, 5'-O-dimethoxytrityl-1',2'-dideoxyribose-3'-[(2-cyanoethyl)-(N, N-diisopropyl)]-phosphoramidite, 18-O-dimethoxytrityl hexaethyleneglycol, 1-[(2-cyanoethyl)-(N,N-diisopropyl)]-phosphoramidite, 12-(4,4'-dimethoxytrityloxy)dodecyl-1-[(2-cyanoethyl)-(N,N-diisopropyl)]-phosphoramidite, 1,3-bis-[5-(4,4'-dimethoxytrityloxy) pentylamido]propyl-2-[(2-cyanoethyl)-(N,N-diisopropyl)]-phosphoramidite, 1-[5-(4, 4'-dimethoxytrityloxy)pentylamido]-3-[5-fluorenomethoxycarbonyloxypentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxy tetramethylrhodamine succinimidyl ester, bis-(4-carboxypiperidinyl)sulfonerhodamine di(succinimidyl ester), 5- and 6-((N-(5-aminopentyl)aminocarbonyl) tetramethylrhodamine, succinimidyl 4-(p-maleimidophenyl)butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. Accordingly, mobility modifiers M may be constructed from such reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996).

In another aspect, (M,D) moieties are constructed from chemical scaffolds used in the generation of combinatorial libraries. For example, the following references describe scaffold compounds useful in generating diverse mobility modifying moieties: peptoids (PCT Publication WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., *Proc. Nat. Acad. Sci. U.S.A.* 90: 6909–6913 (1993)), vinylogous polypeptides (Hagihara et al., *J. Am. Chem. Soc.* 114: 6568 (1992)), nonpeptidal peptidomimetics with a β-D-glucose scaffolding (Hirschmann, R. et al., *J. Am. Chem. Soc.* 114: 9217–9218 (1992)), analogous organic syntheses of small compound libraries (Chen, C. et al., *J. Am. Chem. Soc.* 116:2661(1994)), oligocarbamates (Cho, C. Y. et al., *Science* 261: 1303(1993)), peptidyl phosphonates (Campbell, D. A. et al., J. Org. Chem. 59:658(1994)); Cheng et al., U.S. Pat. No. 6,245,937; Heizmann et al., "Xanthines as a scaffold for molecular diversity," *Mol. Divers.* 2:171–174 (1997); Pavia et al., *Bioorg. Med. Chem.* 4:659–666 (1996); Ostresh et al., U.S. Pat. No. 5,856,107; Gordon, E. M. et al., *J. Med. Chem.* 37:1385 (1994); and the like. Preferably, in this aspect, D is a substituent on a scaffold and M is the rest of the scaffold.

In another aspect, mobility-modifying moiety, M, comprises an alkylene or aralkylene group, the latter comprising a divalent aliphatic group having about 1 to about 2 aliphatic regions and about 1 to about 2 aromatic regions, generally benzene, where the groups may be substituted or unsubstituted, usually unsubstituted, comprising from 2 to about 16, more usually 2 to about 12, carbon atoms. The mobility-modifying moiety may be used to link one or more fluorescers to a monomeric unit, e.g., a nucleotide. The mobility-modifying moiety may terminate in a carboxy, hydroxy or amino group, forming an ester or amide upon conjugation. By varying the substituents on the fluorescer(s), one can vary the mass in units of at least about 5 or more, usually at least about 9. To provide further variation, a thiosuccinimide group may be employed to join alkylene or aralkylene groups, such that the total number of carbon atoms may be in the range of 2 to about 30, more usually 2 to about 20. Instead of or in combination with the above groups, and to add hydrophilicity, alkyleneoxy groups may be used.

In some embodiments, the molecular tags need not be charged, but merely differ in mass. Thus, the same or similar monomers can be used, where the functionalities are neutral or converted to neutral moieties, such as esters and amides of carboxylic acids. Also, the molecular tags may be varied by isotopic substitution, such as $^2$H, $^{18}$O, $^{14}$C, etc.

Diversity in sets of probes or e-tags can also be achieved via the chemical and optical characteristics of the label, the use of energy transfer complexes, and variations in the chemical nature of the mobility-modifying moiety which affect mobility, e.g. via folding, interaction with the solvent and ions in the solvent, and the like.

It may be advantageous to effect the release of multiple molecular tag reporters for a binding event involving an individual target molecule. In a sense, this results in an amplification of signal. Accordingly, a plurality of molecular tags is attached to the probe oligonucleotide. For example, each probe oligonucleotide can have attached moieties that result in the release of from 2–300, preferably from 2–100, and more preferably from about 2 to about 10 molecules of detectable moieties per molecule.

C. Enzymes

Recognition duplexes are cleaved by a cleavage agent comprising either a chemical or a protein nuclease that requires a double stranded structure for cleavage to occur. A wide variety of cleavage agents may be used with the method of the invention. Chemical nucleases are described in the following references: Sigman et al., "Chemical nucleases: new reagents in molecular biology," *Annu. Rev. Biochem.* 59: 207–236 (1990); and Thuong et al., "Sequence-specific recognition and modification of double-helical DNA by oligonucleotides," *Angew. Chem. Int. Ed. Engl.* 32: 666–690 (1993). Generally, the oligonucleotide-based chemical nucleases have three components: i) an oligonucleotide moiety for sequence-specific binding, ii) a cleavage moiety, and iii) a linking moiety for attaching the oligonucleotide to the cleavage moiety. Sequence specific binding has been achieved by the formation of a Watson-Crick duplex with a single stranded target, by the formation of a "D-loop" with a double stranded target, and by the formation of a triplex structure with a double stranded target. In all of these cases, the oligonucleotide moiety defines the recognition site of the chemical nuclease.

The cleavage moiety may linked to the 5' end, the 3' end, to both ends, or to internal bases of the oligonucleotide moiety; thus, for oligonucleotide-based chemical nucleases, the recognition site may be separate from its cleavage site(s). The cleavage moieties for DNA targets typically are one of two types: a chemically activated agent for generating a diffusable radical, e.g. hydroxyl, that effects cleavage, or a tethered protein nuclease. Preferred cleavage enzymes include native or modified DNA polymerases having 5'-nuclease activity but lacking synthetic activity. Preferably, the enzyme is of sufficient activity to rapidly execute an entire cleavage reaction, including recognition, cleavage and release, giving high turnover (number of cleavages per analyte structure) and is highly selective for the desired cleavage site within the structure. Such enzymes known in the art include the Cleavase™ enzymes produced by Third Wave Technologies, the FEN-1 (Flap EndoNuclease) endonucleases (including RAD2 and XPG (Xeroderma Pigmentosa-complementation group G) proteins), Taq DNA polymerase, and *E. coli* DNA polymerase I. The FEN1, RAD2, and XPG proteins are involved in DNA repair, and have been shown to favor the cleavage of structures that resemble a displaced 5' strand. Similar DNA repair enzymes have been isolated from single cell and higher eukaryotes and from archaea, and there are related DNA repair proteins in eubacteria. Similar 5' nucleases have also been associated with bacteriophage such as T5 and T7.

Thermostable DNA polymerases can be modified to reduce or eliminate synthetic activity, e.g. by proteolysis, where the enzyme is physically cleaved with proteolytic enzymes to produce fragments that are deficient in synthetic activity but retain 5' nuclease activity; or recombinantly, by cloning and amplifying a thermostable DNA polymerase and then deleting the polymerase portion of the gene, e.g. by deletion of the encoding genetic material, by introduction of a translational stop codon by mutation or frame shift, or by proteolytic treatment, as above. Such modified polymerases can be tested for the presence of synthetic and 5' nuclease activity, as described in Hall et al,. U.S. Pat. No. 6,348,314.

The synthetic activity of a thermostable DNA polymerase can also be reduced by chemical means, by employing conditions which preferentially inhibit the synthetic activity of the polymerase. For example, concentrations of $Mg^{+2}$ greater than 5 mM inhibit the polymerization activity of the native DNAP Taq. The synthetic activity of thermostable polymerases can also be eliminated by exposure of the polymerase to extreme heat (typically 96–100° C.) for extended periods of time (20 minutes or more). Preferably, however, the enzyme is physically modified. As noted above, a variety of such enzymes are known and commercially available.

Preferably, recognition duplexes are cleaved with a protein nuclease that has well defined and repeatable cleavage properties. Suitable nucleases for use with the invention include, but are not limited to, restriction endonucleases and repair enzymes. Suitable nucleases for use with the invention include Fpg protein, endonuclease III (Nth) protein, AlkA protein, Tag protein, MPG protein, uracil-DNA glycosylase (UDG protein), MutY protein, T4 endonuclease V, cv-PDG protein, 8-oxo-guanine DNA glycosylase (hOGG1), FEN-1, human AP endonuclease, lambda exonuclease, RNase H, and the like. Such enzymes are commercially available from multiple vendors, New England Biolabs (Beverly, Mass.) and Trevigen Corp. (Gaithersburg, Md.). Many restriction endonucleases are suitable for use with the invention. Restriction endonucleases that can efficiently cleave at the end of a duplex are preferred so that released molecular tags contains as few nucleotides as possible from the recognition duplex. Preferred restriction endonucleases include Tsp509 I, Nla III, BssK1, Dpn II, Mbo I, Sau 3A I, Mbo II, Ple I, Mnl I, Alw I, and the like, which are available from New England Biolabs (Beverly, Mass.). Preferably, thermal stable variants of nucleases are employed so that assay reaction temperature can be conducted in the range of from 40° C. to 70° C., and more preferably, in the range of from 40° C. to 65° C., and still more preferably, in the range of from 50° C. to 65° C.

A "DNA repair enzyme" is an enzyme that is a component of a DNA repair machinery, which enzyme is not a DNA polymerase. DNA repair enzymes include, for example, the enzymes participating in base excision repair (BER), nucleotide excision repair (NER) and mismatch repair (MMR). For a review of the role of chemical structure in determination of repair enzyme substrate specificity and mechanism, see Singer and Hang, Chapter 2, DNA and Free Radicals: Techniques, Mechanisms & Applications (Aruoma and Halliwell ed.), OICA International, 1998.

The base excision repair (BER) enzymes excise free bases from damaged DNA. The substrates for BER enzymes are mainly small DNA lesions such as oxidatively damaged bases, alkylation adducts, deamination products and certain types of single base mismatches. Base excision repair enzymes include DNA glycosylases such as Fpg protein, Nth protein, AlkA protein, Tag protein, MPG protein, UDG protein, Mut Y protein, T4 endonuclease V, and cv-PDG. These specific enzymes act at the first step of the BER pathway, in which DNA glycosylase hydrolyses the N-glycosylic bond connecting the altered base and the sugar-phosphate backbone, releasing a free base. The remaining abasic (AP) site is nicked by an AP endonuclease. Some glycosylases have associated AP lyase activity, which creates strand breaks 3' to an AP site. Fpg and NTh proteins are DNA glycosylases/AP lyases recognizing and excising major purine and pyrimidine products of oxidative damage to DNA, respectively. AlkA protein removes a variety of damaged bases induced by alkylation, deamination or oxidation. Tag protein is a DNA glycosylase excising 3-methyladenosine and 3-methylguanine. These enzymes are active on damages present in double stranded DNA substrates. UDG (uracil-DNA glycosylase) removes uracil from both double and single-stranded DNA. MutY protein is a DNA glycosylase/AP lyase which recognizes adenine-guanine or adenine-cytosine mismatches and excises adenine. All of the above enzymes are of E. Coli origin.

In addition, human MPG (methylpurine glycosylase) recognizes alkylation, deamination, and oxidatively damaged bases in double stranded DNA. T4 endonuclease V is a glycosylase/AP lyase that is specific for UV light-induced cis-syn cyclobutane pyrimidine dimer (CPDs). Chlorella virus pyrimidine dimer glycosylase (cv-PDG) is specific not only for the cis-syn CPDs, but also for the trans-syn-II isomers. Typical glycosylases/lyases are listed in Table 1.

TABLE 1

Glycosylases and Repair Enzymes with Nuclease Activity

| Enzyme | Synonyms | Substrates | AP Lyase Activity |
|---|---|---|---|
| Fpg protein | E. coli Fapy-DNA glycosylase, 8-oxoguanine DNA glycosylase | 8-oxoguanine and formamidopyrimidines (FAPY-adenine, FAPY-guanine), $N^7$ or $C^8$ alkylated guanines modified by ring opening, 5-hydroxycytosine, 5-hydroxyuracil | + |
| Nth protein | E. coli Endonuclease III, thymine glycol-DNA glycosylase | 5,6-dihydrothymine, 5-hydroxy-5-methylhydantoin, 5-hydroxy-6-uracil, alloxan, 5-hydroxy-6-hydrouracil, thymine glycol, cytosine glycol, urea residues, pyrimidine hydrates, 5-hydroxycytosine. | + |
| AlkA protein | E. coli 3-methyladenine-DNA glycosylase II | 3-alkyladenine, 7-alkylguanine, 3-alkylguanine, $O^2$-alkylpyrimidines, formyl uracil, hypoxanthine, hydroxymethyl uracil, adenine and guanine | − |
| Tag protein | E. coli 3-methyladenine-DNA glycosylase I | 3-methyladenine and 3-methylguanine | − |
| MPG protein | Human 3-methyladenine-DNA glycosylase, ANPG protein, AAG protein, NMPG protein | 3-methyladenine, 7-methylguanine, 3-methylguanine, ethenoadenine, ethenoguanine, hypoxanthine and chloroethylnitrosourea adducts | − |
| UDG protein | E. coli Ung protein | uracil and 5-hydroxyuracil | + |

TABLE 1-continued

Glycosylases and Repair Enzymes with Nuclease Activity

| Enzyme | Synonyms | Substrates | AP Lyase Activity |
|---|---|---|---|
| Mut Y protein | E. coli MicA protein | adenine-guanine or adenine cytosine mismatches | + |
| T4 endonuclease V | PD-DNA glycosylase | cis-syn cyclobutane pyrimidine dimers | + |
| cv-PDG | | cis-syn and trans-syn-II cyclobutane pyrimidine dimers | + |

The substrates for the NER enzymes are a wide variety of bulky distortive DNA adducts and certain nondistortive types of DNA damage. The damage during NER is released as a part of an oligonucleotide fragment. Examples of nucleotide excision repair enzymes include the E. coli UvrABC exonuclease, which recognizes a wide spectrum of genotoxic DNA adducts. In addition to pyrimidine dimers and 6–4 photoproducts, the substrates of the Uvr ABC exonuclease include adducts of psoralen, 4-nitroquinoline oxide, cisplatin, benzo[a]pyrene diolepoxide (BPDE), aflatoxin B1, N-acetoxy-2-acetylaminofluorene, 7,12-dimethylbenzo[a]anthracene diolepoxide, mitomycin C, and many others. The Uvr ABC exonuclease complex consists of three proteins (UvrA, UvrB, and UvrC), which recognize and release the damage-containing fragment in a multi-step bimodal incision reaction. The excised oligonucleotide has a size of 12–13 nucleotides. However, in human cells, the damaged sequence is released within a 24–32 mer oligonucleotide.

The third major DNA repair mechanism, MMR, corrects single mispaired nucleotides and short loops. In addition to the excision repair systems, other important repair pathways, including direct reversal of DNA damage ($O^6$-methylguanine-DNA methyltransferase and DNA photolyase) and double-strand break/recombination repair, are also fundamental factors in maintaining genetic stability.

Particularly preferred protein nucleases from cleaving recognition duplexes include Fpg protein, Mut Y protein, hOGG1 protein, Nth protein (endonuclease III), human AP endonuclease, RNase H, and lambda endonuclease. Embodiments of the invention employing two of these nucleases are illustrated in FIGS. 4A–B.

D. Analytes

As discussed above, the analyte is typically a biochemical marker, such as a cell surface receptor or other cell protein, that is associated with a disease state. More generally, the analyte can be any biomolecule whose presence or absence in a sample is desired to be assayed, and for which a specific binding molecule, such as an antibody, is available or can be produced. In addition to a receptor or other protein, analytes may include an epitope (antigenic portion) of such a receptor or protein, a carbohydrate, a nucleic acid, or other biomolecule.

The sample may be a tissue sample, e.g. fixed paraffin-embedded tissue, frozen tissue sections, a cultured or uncultured cell sample, or body fluid sample. Tissue samples may be obtained from resected tissue or biopsy material, which may be prepared using standard techniques routinely employed by surgical pathologists, e.g. frozen or paraffin-fixed. See e.g. Wang et al., 2002, for a review of preparation of tissue microarrays, or Hoos et al., 2001, for a discussion of tissue cyroarrays. Tissue samples may be homogenized or otherwise prepared for screening by well known techniques such as sonication, mechanical disruption, chemical lysis, such as detergent lysis, or combinations thereof.

Examples of body fluid samples include blood, urine, lymph fluid, cerebral spinal fluid, amniotic fluid, vaginal fluid and semen. Cells may be isolated from fluid samples by techniques such as centrifugation. For example, blood plasma may be separated from blood cells, so that either or both of these components can be screened separately.

Preferably, the prepared sample is suspended in a buffer, under conditions appropriate for hybridization of the component oligonucleotides and activity of the enzyme, as described above.

In one embodiment, the sample or samples are derived from tissue libraries of clinical origin, which are frequently limited in size and/or availability. Because the assays can be carried out in a multiplexed format, i.e. assaying for many analytes simultaneously, and can generate multiple detectable signals per analyte, such scarce samples can be conserved.

VII. Preparation of Assay Components

Chemical conjugates of antibodies or other biomolecules can be prepared using techniques and materials known to those of skill in the art, such as described, for example, in Hermanson, BIOCONJUGATE TECHNIQUES, (Academic Press, 1996), pp. 460–483; March, ADVANCED ORGANIC CHEMISTRY $4^{th}$ Ed., (Wiley 1992); Green and Wuts, PROTECTIVE GROUPS IN ORGANIC SYNTHESIS $2^{nd}$ Ed. (Wiley 1991). The procedures described herein for synthesizing the compounds of the invention may include steps of protection and deprotection, purification and characterization, as are well known in the chemical arts.

A. Synthesis of Ligand-Oligonucleotide Conjugates (Binding Compositions)

In accordance with one embodiment of the present invention, a binding agent, such as an antibody, is conjugated to an oligonucleotide, either directly or via a flexible linker, as noted above. Direct conjugation may be carried out using methods such as described in Hendrickson et al., Nucleic Acids Res. 23(3):522–29 (1995), which are modifications of conventional enzyme-antibody linking protocols such as described in Hermanson, pp. 460–483. In general, the components are linked via a heterobiofunctional linking reagent. Reactive moieties on the molecules, e.g. amine groups of antibodies, are used as initial attachment points. These procedures can be used by those of skill in the art for other biomolecules, such as other proteins, containing similar reactive groups.

The oligonucleotide can be provided with a terminal primary aliphatic amine by empoying, in the final coupling step, the reagent Aminolink2™, a phosphoramidite coupling reagent having a trifluoroacetyl-protected amino side chain, available from Applied Biosystems, Foster City, Calif. (see e.g. L. M. Smith et al., Nucleic Acids Res. 15, 6181 (1987); B. S. Sproat et al., Nucleic Acids Res. 19:3749 (1991)).

Figure 7:
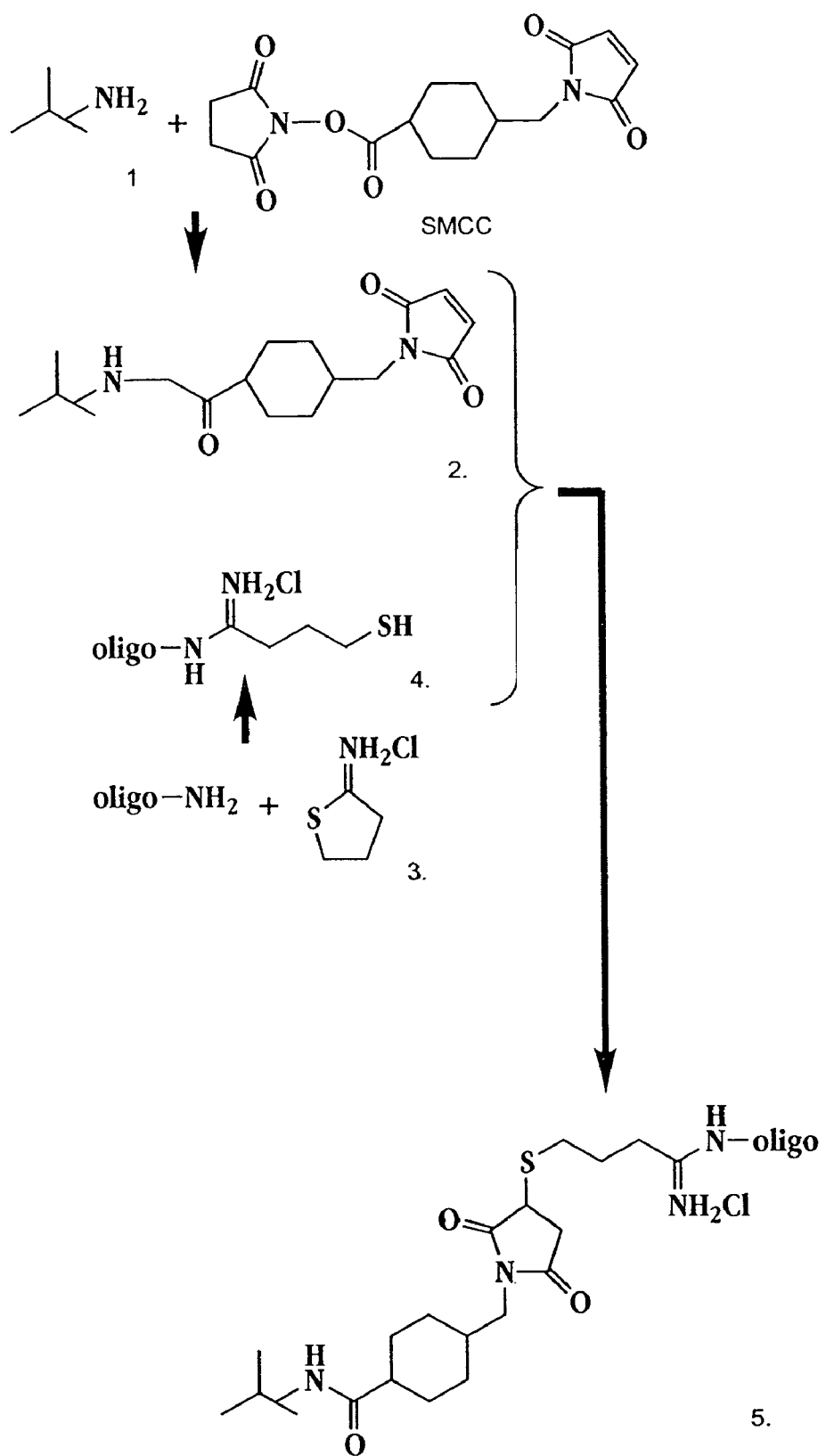
FIG. 7 shows a synthetic scheme for preparing an antibody-oligonucleotide conjugate.

In one conjugation scheme, either component is derivatized with a reactive maleimide group, by reaction with SMCC(N-succinimidyl-4-(maleimidomethyl cyclohexane)-1-carboxylate) or its more water-soluble analog, sulfo-SMCC, available from Pierce Biotechnology (Rockford, Ill.), both of which are widely used in bioconjugation chemistry. The reagent contains, at one terminus, an NHS ester group, which is displaced by an amine on the binding agent or oligonucleotide, and at the other terminus, a maleimide group (see FIG. 7). In FIG. 7, an amine group on the antibody 1 is reacted with SMCC to produce the maleimide derivative 2. An active amine on the oligonucleotide 3, which may be prepared as noted above, is reacted with 2-aminothiolane, also known as Traut's reagent, to produce a terminal thiol group attached to the oligonucleotide (4). Reaction of the activated components 2 and 4 produces the conjugate 5.

In a variation on this procedure, the thiolating reagent SATA (N-succinimidyl-S-acetylthioacetate) can be used to produce a protected thiol functionality on either component, which can be stored and deprotected prior to use.

Ligand-oligonucleotide conjugates with flexible linkers between these two components can be formed by, for example, employing an oligonucleotide having an attached linker, such as a PEG chain. Use of derivatized PEG polymers or oligomers for preparation of conjugates with biomolecules, such as proteins, lipids, or oligonucleotides, is well known in the art. For example, a heterobifunctional PEG oligomer, having an NHS ester at one terminus and a protected hydrazide at the other terminus, is described by Zalipsky (1993). Preparation of conjugates of oligonucleotides with PEG or other non-nucleotide polymers is described, for example, in U.S. Pat. No. 5,470,705 (Grossman et al.), U.S. Pat. No. 4,904,582 (Tullis), and U.S. Pat. No. 5,672,662 (Harris et al.).

In one approach, an oligonucleotide is prepared by standard phosphoramidite chemistry and terminated with a phosphoramidite monomer having an attached PEG oligomer which terminates in a DMT ether, as described in Grossman et al., cited above. The DMT ether is then deprotected to give the alcohol, which can then be converted to an NHS ester, which can be reacted with an amine-containing antibody or other binding agent to give the ligand-linker-oligonucleotide conjugate.

Once prepared, the conjugates may be purified, for example, by gel filtration chromatography, as described in Hendrickson. An especially convenient method of purifying antibody-containing conjugates employs affinity chromatography, particularly nickel-chelate affinity chromatography, as described in Hermanson, pp 486–7. Affinity chromatography methods are most effective when the oligonucleotide is used in excess for the conjugation, so that little unconjugated antibody is present.

B. Synthesis of Oligonucleotide-Tag Conjugates (Detection Probes)

Preferably, the helper probe and detection probe comprise synthetic oligonucleotides produced using conventional techniques. The mobility-modifying region and detectable label of detection probes are preferably attached to the oligonucleotide portion by forming a phosphoramidite precursor that may be coupled to oligonucleotide portion in the final step of a probe's synthesis. The detection probes can be easily and effectively prepared via assembly on a solid phase support using standard phosphoramidite chemistries, as described, for example, in Handbook of Molecular Probes and Research Products, 8$^{th}$ edition (Molecular Probes, Inc., Eugene, Oreg., 2002); Beaucage and Iyer, Tetrahedron, 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679; and the like. Many of these chemistries allow components of the detection probe to be conveniently synthesized on an automated DNA synthesizer, e.g. an Applied Biosystems, Inc. (Foster City, Calif.) model 392 or 394 DNA/RNA Synthesizer.

In a general approach, any of a variety of detectably labeled phosphoramidate monomers can be prepared and incorporated into an oligonucleotide during standard synthesis, thus incorporating a molecular tag into the oligonucleotide probe. The monomers can be prepared from commercially available, variously substituted fluorescent dyes. For example, in one approach, the phenolic hydroxyl groups of commercially available 6-carboxy fluorescein are protected as esters by reaction with an anhydride. The carboxyl functionality is then activated in situ via formation of an N-hydroxy succinimide (NHS) ester, which is then reacted with an amino alcohol. The free hydroxyl group of the product is phosphitylated to generate the phosphoramidite monomer. Varied molecular tag moieties can be produced by varying the amino alochol. In particular, a symmetrical bis-amino alcohol linker can be used, followed by coupling of the free amine with any of a a variety of carboxylic acid derivatives, prior to the phosphitylation reaction.

In another approach, 5-aminofluorescein is reacted with a large excess of a diacid dichloride, to favor the formation of the monoacylated product, which undergoes hydrolysis to a carboxylic acid on workup. The carboxylic acid then undergoes the series of reactions described above for formation of the phosphoramidite monomer. In this case, a variety of diacid as well as a variety of amino alcohols can be employed, to generate a diverse set of molecular tags.

It is claimed:

1. A method of detecting the presence or absence of a plurality of analytes in a sample, the method comprising the steps of:
   providing for each analyte a binding composition having a oligonucleotide label;
   providing for each oligonucleotide label a reagent pair, consisting of a detection probe specific for the oligonucleotide label in a given region, and a helper probe specific for the oligonucleotide label at a location adjacent to the given region, the detection probe having a molecular tag attached, said tag having distinct optical or separation properties with respect to molecular tags of other detection probes;
   combining the binding compositions with the sample so that analyte complexes are formed between the analytes and their respective binding compositions;
   removing binding compositions that do not form analyte complexes;
   combining under hybridization conditions: the analyte complexes, the reagent pairs corresponding to the oligonucleotide label of each binding composition, and a nuclease, such that the helper probe and the detection probe specific for each oligonucleotide label form a cleavage structure with said oligonucleotide label that is recognized by the nuclease, and the nuclease cleaves the structure to release the molecular tag; and
   separating and identifying the released molecular tags to determine the presence or absence of the plurality of analytes.

2. The method of claim 1, wherein said cleavage structure is not formed by the helper probe and detection probe, under said hybridization conditions, in the absence of the corresponding oligonucleotide label.

3. The method of claim 1, wherein said conditions are such that detection probe hybridized to said oligonucleotide label is in equilibrium with unhybridized detection probe, such that cleaved detection probe is repeatedly displaced from said oligonucleotide label by additional detection probe.

4. The method of claim 1, wherein
at least one analyte has first and second binding sites;
the binding composition provided for said analyte comprises a binding agent that is specific for said first binding site; and
the helper probe provided for said binding composition is linked to a second binding agent specific for said second binding site.

5. The method of claim 4, wherein the binding composition comprises a flexible linker between said binding agent and the oligonucleotide label, and the helper probe is linked to said second binding agent via a flexible linker.

6. The method of claim 1, wherein the binding composition comprises an antibody.

7. The method of claim 1, wherein the molecular tags are fluorescently labeled.

8. The method of claim 1, wherein each released tag has an electrophoretic mobility, upon release, which is distinct from electrophoretic mobility of released tags from other detection probes.

9. The method of claim 1, wherein the sample is derived from a clinical tissue library.

10. A method of detecting the presence or absence of a plurality of analytes in a sample, the method comprising the steps of:
providing for each analyte a binding pair comprising a first binding composition having a first oligonucleotide label and a second binding composition having a second oligonucleotide label, the first oligonucleotide label and the second oligonucleotide label being complementary to one another in a first region so that whenever the first binding composition and the second binding composition bind to the same analyte a duplex is formed;
providing for each first oligonucleotide label and second oligonucleotide label a detection probe specific for either the first oligonucleotide label or the second oligonucleotide label at a location adjacent to the region, the detection probe having a molecular tag attached by a cleavable linkage, the molecular tag of each detection probe having one or more physical and/or optical characteristics distinct from those of molecular tags attached to other detection probes so that upon separation each molecular tag forms a distinguishable peak in a separation profile;
combining the binding pairs with the sample so that analyte complexes are formed between the analytes and their respective binding pairs and so that duplexes form between each first and second oligonucleotide labels;
removing binding pairs that do not form analyte complexes;
combining under hybridization conditions: a nuclease, the analyte complexes, and the detection probes of each binding pair, such that the detection probes specific for each first or second oligonucleotide label form a cleavage complex recognized by the nuclease and such that the nuclease cleaves and releases the molecular tags from cleavage complexes; and
separating and identifying the released molecular tags to detect the presence or absence of the plurality of analytes.

* * * * *